United States Patent
Eboigbodin et al.

(10) Patent No.: US 11,008,625 B2
(45) Date of Patent: May 18, 2021

(54) DETECTION OF NUCLEIC ACIDS BY STRAND INVASION BASED AMPLIFICATION

(71) Applicant: AIDIAN OY, Espoo (FI)

(72) Inventors: Kevin Eboigbodin, Masala (FI); Mirko Brummer, Lohja (FI)

(73) Assignee: AIDIAN OY, Espoo (FI)

( * ) Notice: Subject to any disclaimer, the term of this patent is extended or adjusted under 35 U.S.C. 154(b) by 189 days.

(21) Appl. No.: 15/038,439

(22) PCT Filed: Nov. 21, 2014

(86) PCT No.: PCT/EP2014/075321
§ 371 (c)(1),
(2) Date: May 20, 2016

(87) PCT Pub. No.: WO2015/075198
PCT Pub. Date: May 28, 2015

(65) Prior Publication Data
US 2016/0289747 A1    Oct. 6, 2016

(30) Foreign Application Priority Data
Nov. 22, 2013 (EP) .................................. 13194118

(51) Int. Cl.
*C12Q 1/689* (2018.01)
*C12Q 1/6844* (2018.01)
*C12Q 1/6818* (2018.01)

(52) U.S. Cl.
CPC ........... *C12Q 1/689* (2013.01); *C12Q 1/6818* (2013.01); *C12Q 1/6844* (2013.01); *C12Q 2600/16* (2013.01)

(58) Field of Classification Search
CPC ...... C12Q 2521/507; C12Q 2537/1373; C12Q 2561/1131; C12Q 1/6844;
(Continued)

(56) References Cited

U.S. PATENT DOCUMENTS

| 5,436,134 A | 7/1995 | Haugland et al. |
| 5,925,517 A | 7/1999 | Tyagi et al. |

(Continued)

FOREIGN PATENT DOCUMENTS

| WO | 199804738 A1 | 2/1998 |
| WO | 199905314 A1 | 2/1999 |

(Continued)

OTHER PUBLICATIONS

Wang et al., "LNA real-time PCR probe quantification of hepatitis B virus DNA," Experimental and Therapeutic Medicine, vol. 3, pp. 503-508. (Year: 2012).*

(Continued)

*Primary Examiner* — Young J Kim
(74) *Attorney, Agent, or Firm* — Norton Rose Fulbright US LLP

(57) ABSTRACT

A method for detecting a target nucleic acid sequence in a sample in the presence of at least protein capable of binding to single-stranded DNA is provided, comprising contacting said sample with at least one oligonucleotide probe comprising a fluorophore, a quencher and a region complementary to said target nucleic acid sequence. The sequence of the oligonucleotide probe comprises at least 20% RNA nucleotides, modified RNA nucleotides and/or PNA nucleotides.

14 Claims, 12 Drawing Sheets

Specification includes a Sequence Listing.

(58) Field of Classification Search
CPC ............ C12Q 2525/125; C12Q 1/6818; C12Q 2525/107; C12Q 2525/113

See application file for complete search history.

(56) References Cited

U.S. PATENT DOCUMENTS

| | | | |
|---|---|---|---|
| 6,214,979 | B1 | 4/2001 | Gelfand et al. |
| 7,241,596 | B2 | 7/2007 | Mayrand |
| 7,435,561 | B2 | 10/2008 | Piepenburg et al. |
| 10,196,684 | B2 * | 2/2019 | Ismagilov ............ C12Q 1/6844 |
| 2002/0061530 | A1 | 5/2002 | Belotserkovskii et al. |
| 2003/0180746 | A1 * | 9/2003 | Kmiec ................ C12Q 1/6806 435/6.14 |
| 2005/0214809 | A1 | 9/2005 | Han |
| 2007/0031845 | A1 * | 2/2007 | DeNise ................ C12Q 1/6876 435/6.12 |
| 2010/0055685 | A1 * | 3/2010 | Saul ...................... C12Q 1/6818 435/6.1 |
| 2012/0157333 | A1 | 6/2012 | Kauppinen |
| 2012/0219945 | A1 | 8/2012 | Lee |
| 2012/0258456 | A1 * | 10/2012 | Armes ............... G01N 21/6428 435/6.11 |
| 2013/0177906 | A1 * | 7/2013 | Li ........................ C12Q 1/6876 435/6.11 |
| 2016/0102343 | A1 | 4/2016 | Filen |

FOREIGN PATENT DOCUMENTS

| | | | | |
|---|---|---|---|---|
| WO | | 199921881 | A1 | 5/1999 |
| WO | | 200034521 | A1 | 6/2000 |
| WO | | 2007096702 | A2 | 8/2007 |
| WO | | 2009150467 | A1 | 12/2009 |
| WO | WO-2009150467 | A1 * | 12/2009 | ........... C12Q 1/6844 |
| WO | | 2014173963 | A1 | 10/2014 |

OTHER PUBLICATIONS

Li et al., "Novel application of Locked Nucleic Acid chemistry for a Taqman assay for measuring diverse human immunodeficiency virus type 1 subtypes," Journal of Virological Methods, vol. 170, pp. 115-120. (Year: 2010).*

Piepenburg et al., "DNA Detection Using Recombination Proteins," PLoS Biology, July, vol. 4, No. 7, e204, pp. 1115-1121. (Year: 2006).*

Product Catalog of LNA from Sigma-Aldrich: [retrieved on-line, retrieval date: Jul. 14, 2020; retrieved from: https://www.sigmaaldrich.com/technical-documents/articles/biology/locked-nucleic-acids-faq.html] (Year: 2020).*

GenBank Accession No. MT114172.1 [retrieved on-line, retrieval date: Jul. 14, 2020; retrieved from: https://www.ncbi.hlm.nih.gov/nucleotide/MT114172.1?report=genbank&log$=nuclalign&blast_rank=2&RID=GW8SBXBF014] (Year: 2020).*

Lalande, Valerie, et al; "Evaluation of a Loop-Mediated Isothermal Amplification Assay for Diagnosis of Clostridium difficile Infections"; Journal of Clinical Microbiology, Jul. 2011, vol. 49, No. 7; p. 2714-2716.

Reynisson et al., "Evaluation of probe chemistries and platforms to improve the detection limit of real-time PCR", Journal of Microbiological Methods, vol. 66. No. 2. Aug. 1, 2006 (Aug. 1, 2006), pp. 206-216, Elsevier. Amsterdam. NL.

Pierce et al., "Rapid detection of sequence variation in Clostridium difficile genes using LATE-PCR with multiple mismatch-tolerant hybridization probes", Journal of Microbiological Methods, vol. 91, No. 2, Nov. 1, 2012 (Nov. 1, 2012), pp. 269-275.

Didenko, V.V.: DNA probes using fluorescence resonance energy transfer (FRET): designs and applications. Biotechniques 2001, 31(5):1106-1116, 1118, 1120-1101.

Lavery et al. J. Biol. Chem. 1992, 267, (13), 9307-9314.

Koshkin et al. LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition.

Yang et al. Synthesis and investigation of deoxyribonucleic acid/locked nucleic acid chimeric molecular beacons.

Shimizu et al. Oligo(2'-O-methyl)ribonucleotides Effective probes for duplex DNA. FEBS Letters, Jun. 1992.

Hoser et al. Strand Invasion Based Amplification (SIBA): A Novel Isothermal DNA Amplification Technology Demonstrating High Specificity and Sensitivity for a Single Molecule of Target Analyte. PLOS One Nov. 2014.

Life Sciences Advanced Technologies catalog, NEC-1-24 NASBA Enzyme Cocktail (wet mix), 2014. (https://lifesci.com/shop/nasba-kits-nasba-products/nasba-kits-components/nasba-enzyme-cocktail-wet-mix/).

Chinese Office Action dated Mar. 30, 2020, including an English Translation, accompanied by the Search Report cited during prosecution of related China Patent Application No. 201480073793.

Common Knowledge, HH Ribozyme, Dec. 31, 1999, pp. 95-98, cited in China OA dated Mar. 30, 2020.

Koshkin et al. LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition, Tetrahedron 54 (1998) 3607-3630.

Yang et al. Synthesis and investigation of deoxyribonucleic acid/locked nucleic acid chimeric molecular beacons, Nucleic Acids Research, 2007, vol. 35, No. 12, 4030-4041.

* cited by examiner

SEQUENCE LISTING

<160> NUMBER OF SEQ ID NOS: 48

<210> SEQ ID NO 1
<211> LENGTH: 16
<212> TYPE: DNA
<213> ORGANISM: Artificial Sequence
<220> FEATURE:
<223> OTHER INFORMATION: DNA PROBE
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (16)..(16)
<223> OTHER INFORMATION: 3' BLACK HOLE QUENCHER 2 TAG

<400> SEQUENCE: 1
agccgatgac taatgc                                                      16

<210> SEQ ID NO 2
<211> LENGTH: 21
<212> TYPE: DNA
<213> ORGANISM: Artificial Sequence
<220> FEATURE:
<223> OTHER INFORMATION: DNA PROBE
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (21)..(21)
<223> OTHER INFORMATION: 3' BLACK HOLE QUENCHER 2 TAG

```
<400> SEQUENCE: 2
acgaaagccg atgactaatg c                                              21

<210> SEQ ID NO 3
<211> LENGTH: 16
<212> TYPE: RNA
<213> ORGANISM: Artificial Sequence
<220> FEATURE:
<223> OTHER INFORMATION: RNA PROBE
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (16)..(16)
<223> OTHER INFORMATION: 3' BLACK HOLE QUENCHER 2 TAG

<400> SEQUENCE: 3
agccgaugac uaaugc                                                    16

<210> SEQ ID NO 4
<211> LENGTH: 21
<212> TYPE: RNA
<213> ORGANISM: Artificial Sequence
<220> FEATURE:
<223> OTHER INFORMATION: RNA PROBE
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 4
acgaaagccg augacuaaug c                                              21

<210> SEQ ID NO 5
<211> LENGTH: 16
<212> TYPE: RNA
<213> ORGANISM: Artificial Sequence
<220> FEATURE:
<223> OTHER INFORMATION: RNA PROBE
<220> FEATURE:
<221> NAME/KEY: misc_feature
<222> LOCATION: (1)..(16)
<223> OTHER INFORMATION: 2'-O-METHYL RNA
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (16)..(16)
<223> OTHER INFORMATION: 3' BLACK HOLE QUENCHER 2 TAG

<400> SEQUENCE: 5
agccgaugac uaaugc                                                    16

<210> SEQ ID NO 6
<211> LENGTH: 21
<212> TYPE: RNA
<213> ORGANISM: Artificial Sequence
<220> FEATURE:
<223> OTHER INFORMATION: RNA PROBE
<220> FEATURE:
<221> NAME/KEY: misc_feature
<222> LOCATION: (1)..(21)
<223> OTHER INFORMATION: 2'-O-METHYL RNA
```

```
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 6
acgaaagccg augacuaaug c                                              21

<210> SEQ ID NO 7
<211> LENGTH: 16
<212> TYPE: RNA
<213> ORGANISM: Artificial Sequence
<220> FEATURE:
<223> OTHER INFORMATION: RNA PROBE
<220> FEATURE:
<221> NAME/KEY: misc_feature
<222> LOCATION: (1)..(16)
<223> OTHER INFORMATION: 2'-FLUORO RNA
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (16)..(16)
<223> OTHER INFORMATION: 3' BLACK HOLE QUENCHER 2 TAG

<400> SEQUENCE: 7
agccgaugac uaaugc                                                    16

<210> SEQ ID NO 8
<211> LENGTH: 21
<212> TYPE: RNA
<213> ORGANISM: Artificial Sequence
<220> FEATURE:
<223> OTHER INFORMATION: RNA PROBE SEQUENCE
<220> FEATURE:
<221> NAME/KEY: misc_feature
<222> LOCATION: (1)..(21)
<223> OTHER INFORMATION: 2'-FLUORO RNA
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 8
acgaaagccg augacuaaug c                                              21

<210> SEQ ID NO 9
<211> LENGTH: 12
<212> TYPE: RNA
<213> ORGANISM: Artificial Sequence
<220> FEATURE:
<223> OTHER INFORMATION: LNA PROBE
<220> FEATURE:
<221> NAME/KEY: misc_feature
<222> LOCATION: (1)..(12)
<223> OTHER INFORMATION: LOCKED NUCLEIC ACID
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (12)..(12)
```

```
<223> OTHER INFORMATION: 3' BLACK HOLE QUENCHER 2 TAG

<400> SEQUENCE: 9
aguugaugug ua                                                          12

<210> SEQ ID NO 10
<211> LENGTH: 14
<212> TYPE: DNA
<213> ORGANISM: Artificial Sequence
<220> FEATURE:
<223> OTHER INFORMATION: PNA PROBE
<220> FEATURE:
<221> NAME/KEY: misc_feature
<222> LOCATION: (1)..(12)
<223> OTHER INFORMATION: PEPTIDE NUCLEIC ACID
<220> FEATURE:
<221> NAME/KEY: misc_feature
<222> LOCATION: (1)..(1)
<223> OTHER INFORMATION: TETRAMETHYLRHODAMINE TAG
<220> FEATURE:
<221> NAME/KEY: misc_feature
<222> LOCATION: (12)..(12)
<223> OTHER INFORMATION: 3' T CONJUGATED TO LYSINE AND BLACK HOLE
      QUENCHER 2 TAG

<400> SEQUENCE: 10
agttgatgtg tact                                                        14

<210> SEQ ID NO 11
<211> LENGTH: 21
<212> TYPE: DNA
<213> ORGANISM: Artificial Sequence
<220> FEATURE:
<223> OTHER INFORMATION: DNA PRIMER SEQUENCE

<400> SEQUENCE: 11
aacaagaagg cgtactcgac c                                                21

<210> SEQ ID NO 12
<211> LENGTH: 20
<212> TYPE: DNA
<213> ORGANISM: Artificial Sequence
<220> FEATURE:
<223> OTHER INFORMATION: DNA PRIMER SEQUENCE

<400> SEQUENCE: 12
agttgatgtg tactgagatc                                                  20

<210> SEQ ID NO 13
<211> LENGTH: 24
<212> TYPE: RNA
<213> ORGANISM: Artificial Sequence
<220> FEATURE:
<223> OTHER INFORMATION: RNA PRIMER
<220> FEATURE:
<221> NAME/KEY: misc_feature
<222> LOCATION: (1)..(24)
<223> OTHER INFORMATION: 2'-FLUORO RNA

<400> SEQUENCE: 13
aguugaugug uacugacuga gauc                                             24

<210> SEQ ID NO 14
<211> LENGTH: 24
<212> TYPE: DNA
<213> ORGANISM: Artificial Sequence
<220> FEATURE:
<223> OTHER INFORMATION: MIXED DNA/RNA PRIMER
<220> FEATURE:
```

```
<221> NAME/KEY: misc_feature
<222> LOCATION: (1)..(20)
<223> OTHER INFORMATION: 2'-FLUORO RNA
<220> FEATURE:
<221> NAME/KEY: misc_feature
<222> LOCATION: (21)..(24)
<223> OTHER INFORMATION: DNA

<400> SEQUENCE: 14
aguugaugug uacugacuga gatc                                           24

<210> SEQ ID NO 15
<211> LENGTH: 61
<212> TYPE: DNA
<213> ORGANISM: Artificial Sequence
<220> FEATURE:
<223> OTHER INFORMATION: STRAND INVASION OLIGONUCLEOTIDE
<220> FEATURE:
<221> NAME/KEY: misc_feature
<222> LOCATION: (48)..(60)
<223> OTHER INFORMATION: 2'-O-METHYL RNA
<220> FEATURE:
<221> NAME/KEY: misc_feature
<222> LOCATION: (61)..(61)
<223> OTHER INFORMATION: INVERTED dTTP

<400> SEQUENCE: 15
ttgtccatag actgctcgac ctgatacacg ttatcgtcca tacggatucg ggaucucaua    60
t                                                                    61

<210> SEQ ID NO 16
<211> LENGTH: 16
<212> TYPE: DNA
<213> ORGANISM: Artificial Sequence
<220> FEATURE:
<223> OTHER INFORMATION: DNA PROBE SEQUENCE
<220> FEATURE:
<221> NAME/KEY: misc_feature
<222> LOCATION: (1)..(1)
<223> OTHER INFORMATION: 6-CARBOXYL-X-RHODAMINE
<220> FEATURE:
<221> NAME/KEY: misc_feature
<222> LOCATION: (16)..(16)
<223> OTHER INFORMATION: 3' BLACK HOLE QUENCHER 2 TAG

<400> SEQUENCE: 16
agttgatgtg tactca                                                    16

<210> SEQ ID NO 17
<211> LENGTH: 16
<212> TYPE: RNA
<213> ORGANISM: Artificial Sequence
<220> FEATURE:
<223> OTHER INFORMATION: RNA PROBE SEQUENCE
<220> FEATURE:
<221> NAME/KEY: misc_feature
<222> LOCATION: (1)..(1)
<223> OTHER INFORMATION: 6-CARBOXYL-X-RHODAMINE
<220> FEATURE:
<221> NAME/KEY: misc_feature
<222> LOCATION: (1)..(16)
<223> OTHER INFORMATION: 2'-FLUORO RNA
<220> FEATURE:
<221> NAME/KEY: misc_feature
<222> LOCATION: (16)..(16)
<223> OTHER INFORMATION: 3' BLACK HOLE QUENCHER 2 TAG

<400> SEQUENCE: 17
aguugaugug uacuga                                                    16
```

```
<210> SEQ ID NO 18
<211> LENGTH: 12
<212> TYPE: RNA
<213> ORGANISM: Artificial Sequence
<220> FEATURE:
<223> OTHER INFORMATION: LNA PROBE SEQUENCE
<220> FEATURE:
<221> NAME/KEY: misc_feature
<222> LOCATION: (1)..(12)
<223> OTHER INFORMATION: LOCKED NUCLEIC ACID
<220> FEATURE:
<221> NAME/KEY: misc_feature
<222> LOCATION: (1)..(1)
<223> OTHER INFORMATION: 6-CARBOXYL-X-RHODAMINE
<220> FEATURE:
<221> NAME/KEY: misc_feature
<222> LOCATION: (12)..(12)
<223> OTHER INFORMATION: DABCYL

<400> SEQUENCE: 18
aguugaugug ua                                                          12

<210> SEQ ID NO 19
<211> LENGTH: 16
<212> TYPE: DNA
<213> ORGANISM: Artificial Sequence
<220> FEATURE:
<223> OTHER INFORMATION: DNA/RNA PROBE/PRIMER
<220> FEATURE:
<221> NAME/KEY: misc_feature
<222> LOCATION: (1)..(10)
<223> OTHER INFORMATION: 2'-FLUORO RNA
<220> FEATURE:
<221> NAME/KEY: misc_feature
<222> LOCATION: (1)..(1)
<223> OTHER INFORMATION: IOWA BLACK FQ
<220> FEATURE:
<221> NAME/KEY: misc_feature
<222> LOCATION: (11)..(11)
<223> OTHER INFORMATION: FLUORESCEIN LINKED TO THE 5' POSITION OF
      THYMIDINE
<220> FEATURE:
<221> NAME/KEY: misc_feature
<222> LOCATION: (12)..(12)
<223> OTHER INFORMATION: 2'-FLUORO RNA
<220> FEATURE:
<221> NAME/KEY: misc_feature
<222> LOCATION: (13)..(16)
<223> OTHER INFORMATION: DNA

<400> SEQUENCE: 19
aguugaugug tactga                                                      16

<210> SEQ ID NO 20
<211> LENGTH: 72
<212> TYPE: DNA
<213> ORGANISM: Artificial Sequence
<220> FEATURE:
<223> OTHER INFORMATION: DNA TARGET NUCLEIC ACID SEQUENCE

<400> SEQUENCE: 20
aacaagaagg cgtactcgac ctgatacacg ttatcgtcca tacggattcg ggatctcagt      60
acacatcaac tg                                                          72

<210> SEQ ID NO 21
<211> LENGTH: 21
<212> TYPE: DNA
<213> ORGANISM: Artificial Sequence
<220> FEATURE:
<223> OTHER INFORMATION: DNA PRIMER SEQUENCE

<400> SEQUENCE: 21
```
aaccaaagtg gagtgttaca a                                              21

<210> SEQ ID NO 22
<211> LENGTH: 16
<212> TYPE: DNA
<213> ORGANISM: Artificial Sequence
<220> FEATURE:
<223> OTHER INFORMATION: DNA PRIMER SEQUENCE

<400> SEQUENCE: 22
tggggcaaaa tattta                                                    16

<210> SEQ ID NO 23
<211> LENGTH: 57
<212> TYPE: DNA
<213> ORGANISM: Artificial Sequence
<220> FEATURE:
<223> OTHER INFORMATION: STRAND INVASION OLIGONUCLEOTIDE
<220> FEATURE:
<221> NAME/KEY: misc_feature
<222> LOCATION: (44)..(56)
<223> OTHER INFORMATION: 2'-O-METHYL RNA
<220> FEATURE:
<221> NAME/KEY: misc_feature
<222> LOCATION: (57)..(57)
<223> OTHER INFORMATION: INVERTED dTTP

<400> SEQUENCE: 23
tcctcctgta cctcgttaca aacaggtgta tttagtacag aagauggauu uaaauat       57

<210> SEQ ID NO 24
<211> LENGTH: 16
<212> TYPE: RNA
<213> ORGANISM: Artificial Sequence
<220> FEATURE:
<223> OTHER INFORMATION: RNA PROBE SEQUENCE
<220> FEATURE:
<221> NAME/KEY: misc_feature
<222> LOCATION: (1)..(1)
<223> OTHER INFORMATION: 6-CARBOXYL-X-RHODAMINE
<220> FEATURE:
<221> NAME/KEY: misc_feature
<222> LOCATION: (1)..(16)
<223> OTHER INFORMATION: 2'-FLUORO RNA
<220> FEATURE:
<221> NAME/KEY: misc_feature
<222> LOCATION: (16)..(16)
<223> OTHER INFORMATION: IOWA BLACK FQ

<400> SEQUENCE: 24
uggggcaaaa uauuua                                                    16

<210> SEQ ID NO 25
<211> LENGTH: 15
<212> TYPE: RNA
<213> ORGANISM: Artificial Sequence
<220> FEATURE:
<223> OTHER INFORMATION: RNA PROBE SEQUENCE
<220> FEATURE:
<221> NAME/KEY: misc_feature
<222> LOCATION: (1)..(1)
<223> OTHER INFORMATION: 5' CYANINE 5 TAG
<220> FEATURE:
<221> NAME/KEY: misc_feature
<222> LOCATION: (1)..(15)
<223> OTHER INFORMATION: 2'-FLUORO RNA
<220> FEATURE:
<221> NAME/KEY: misc_feature
<222> LOCATION: (15)..(15)
<223> OTHER INFORMATION: 3' IOWA BLACK RQ TAG

```
<400> SEQUENCE: 25 ugggggcaaaa uauuu                                                    15

<210> SEQ ID NO 26
<211> LENGTH: 66
<212> TYPE: DNA
<213> ORGANISM: Artificial Sequence
<220> FEATURE:
<223> OTHER INFORMATION: TARGET SEQUENCE

<400> SEQUENCE: 26
aaccaaagtg gagtgttaca aacaggtgta tttagtacag aagatggatt taaatatttt    60
gcccca                                                               66

<210> SEQ ID NO 27
<211> LENGTH: 18
<212> TYPE: DNA
<213> ORGANISM: Artificial Sequence
<220> FEATURE:
<223> OTHER INFORMATION: DNA PRIMER SEQUENCE

<400> SEQUENCE: 27
ctggcgatat tggtgttt                                                  18

<210> SEQ ID NO 28
<211> LENGTH: 16
<212> TYPE: DNA
<213> ORGANISM: Artificial Sequence
<220> FEATURE:
<223> OTHER INFORMATION: DNA PRIMER SEQUENCE

<400> SEQUENCE: 28
accgcaggaa acgttg                                                    16

<210> SEQ ID NO 29
<211> LENGTH: 63
<212> TYPE: DNA
<213> ORGANISM: Artificial Sequence
<220> FEATURE:
<223> OTHER INFORMATION: STRAND INVASION OLIGONUCLEOTIDE
<220> FEATURE:
<221> NAME/KEY: misc_feature
<222> LOCATION: (47)..(62)
<223> OTHER INFORMATION: 2'-O-METHYL RNA
<220> FEATURE:
<221> NAME/KEY: misc_feature
<222> LOCATION: (63)..(63)
<223> OTHER INFORMATION: INVERTED dTTP

<400> SEQUENCE: 29
tcctcctctt cctttgttta tggggtcgtt ctacattgac agaatccuca guuuuucaac    60
gat                                                                  63

<210> SEQ ID NO 30
<211> LENGTH: 13
<212> TYPE: RNA
<213> ORGANISM: Artificial Sequence
<220> FEATURE:
<223> OTHER INFORMATION: RNA PROBE SEQUENCE
<220> FEATURE:
<221> NAME/KEY: misc_feature
<222> LOCATION: (1)..(1)
<223> OTHER INFORMATION: 6-CARBOXYL-X-RHODAMINE TAG
<220> FEATURE:
<221> NAME/KEY: misc_feature
<222> LOCATION: (1)..(13)
<223> OTHER INFORMATION: 2'-FLUORO RNA
```

```
<220> FEATURE:
<221> NAME/KEY: misc_feature
<222> LOCATION: (13)..(13)
<223> OTHER INFORMATION: IOWA BLACK FQ TAG

<400> SEQUENCE: 30
accgcaggaa acg                                                      13

<210> SEQ ID NO 31
<211> LENGTH: 86
<212> TYPE: DNA
<213> ORGANISM: Salmonella typhimurium

<400> SEQUENCE: 31
tgaatatcgt actggcgata ttggtgttta tggggtcgtt ctacattgac agaatcctca   60
gtttttcaac gtttcctgcg gtactg                                        86

<210> SEQ ID NO 32
<211> LENGTH: 16
<212> TYPE: RNA
<213> ORGANISM: Artificial Sequence
<220> FEATURE:
<223> OTHER INFORMATION: RNA PROBE SEQUENCE
<220> FEATURE:
<221> NAME/KEY: misc_feature
<222> LOCATION: (1)..(1)
<223> OTHER INFORMATION: 6-CARBOXYL-X-RHODAMINE
<220> FEATURE:
<221> NAME/KEY: misc_feature
<222> LOCATION: (1)..(16)
<223> OTHER INFORMATION: 2'-O-METHYL RNA
<220> FEATURE:
<221> NAME/KEY: misc_feature
<222> LOCATION: (16)..(16)
<223> OTHER INFORMATION: 3' BLACK HOLE QUENCHER 2 TAG

<400> SEQUENCE: 32
aguugaugug uacuca                                                   16

<210> SEQ ID NO 33
<211> LENGTH: 21
<212> TYPE: DNA
<213> ORGANISM: Artificial Sequence
<220> FEATURE:
<223> OTHER INFORMATION: DNA PRIMER SEQUENCE

<400> SEQUENCE: 33
gtgtacagag catttaagat t                                             21

<210> SEQ ID NO 34
<211> LENGTH: 21
<212> TYPE: DNA
<213> ORGANISM: Artificial Sequence
<220> FEATURE:
<223> OTHER INFORMATION: TARGET DNA SEQUENCE

<400> SEQUENCE: 34
gcattagtca tcggctttcg t                                             21

<210> SEQ ID NO 35
<211> LENGTH: 21
<212> TYPE: DNA
<213> ORGANISM: Artificial Sequence
<220> FEATURE:
<223> OTHER INFORMATION: DNA/RNA PROBE
<220> FEATURE:
<221> NAME/KEY: misc_feature
<222> LOCATION: (1)..(1)
```

```
<223> OTHER INFORMATION: 5' TETRAMETHYLRHODAMINE TAG
<220> FEATURE:
<221> NAME/KEY: misc_feature
<222> LOCATION: (1)..(1)
<223> OTHER INFORMATION: RNA
<220> FEATURE:
<221> NAME/KEY: misc_feature
<222> LOCATION: (7)..(7)
<223> OTHER INFORMATION: RNA
<220> FEATURE:
<221> NAME/KEY: misc_feature
<222> LOCATION: (11)..(11)
<223> OTHER INFORMATION: RNA
<220> FEATURE:
<221> NAME/KEY: misc_feature
<222> LOCATION: (15)..(15)
<223> OTHER INFORMATION: RNA
<220> FEATURE:
<221> NAME/KEY: misc_feature
<222> LOCATION: (19)..(19)
<223> OTHER INFORMATION: RNA
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 35
acgaaagccg atgactaaug c                                             21

<210> SEQ ID NO 36
<211> LENGTH: 22
<212> TYPE: DNA
<213> ORGANISM: Artificial Sequence
<220> FEATURE:
<223> OTHER INFORMATION: DNA/RNA PROBE
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (1)..(1)
<223> OTHER INFORMATION: RNA
<220> FEATURE:
<221> NAME/KEY: misc_feature
<222> LOCATION: (3)..(3)
<223> OTHER INFORMATION: RNA
<220> FEATURE:
<221> NAME/KEY: misc_feature
<222> LOCATION: (5)..(5)
<223> OTHER INFORMATION: RNA
<220> FEATURE:
<221> NAME/KEY: misc_feature
<222> LOCATION: (7)..(7)
<223> OTHER INFORMATION: RNA
<220> FEATURE:
<221> NAME/KEY: misc_feature
<222> LOCATION: (9)..(9)
<223> OTHER INFORMATION: RNA
<220> FEATURE:
<221> NAME/KEY: misc_feature
<222> LOCATION: (11)..(11)
<223> OTHER INFORMATION: RNA
<220> FEATURE:
<221> NAME/KEY: misc_feature
<222> LOCATION: (13)..(13)
<223> OTHER INFORMATION: RNA
<220> FEATURE:
<221> NAME/KEY: misc_feature
<222> LOCATION: (15)..(15)
<223> OTHER INFORMATION: RNA
<220> FEATURE:
<221> NAME/KEY: misc_feature
<222> LOCATION: (17)..(17)
<223> OTHER INFORMATION: RNA
<220> FEATURE:
<221> NAME/KEY: misc_feature
```

```
<222> LOCATION: (19)..(19)
<223> OTHER INFORMATION: RNA
<220> FEATURE:
<221> NAME/KEY: misc_feature
<222> LOCATION: (21)..(21)
<223> OTHER INFORMATION: RNA
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 36
tacgaaagcc gatgactaau gc                                              22

<210> SEQ ID NO 37
<211> LENGTH: 21
<212> TYPE: DNA
<213> ORGANISM: Artificial Sequence
<220> FEATURE:
<223> OTHER INFORMATION: DNA/RNA PROBE
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (1)..(3)
<223> OTHER INFORMATION: RNA
<220> FEATURE:
<221> NAME/KEY: misc_feature
<222> LOCATION: (5)..(7)
<223> OTHER INFORMATION: RNA
<220> FEATURE:
<221> NAME/KEY: misc_feature
<222> LOCATION: (9)..(11)
<223> OTHER INFORMATION: RNA
<220> FEATURE:
<221> NAME/KEY: misc_feature
<222> LOCATION: (13)..(15)
<223> OTHER INFORMATION: RNA
<220> FEATURE:
<221> NAME/KEY: misc_feature
<222> LOCATION: (17)..(19)
<223> OTHER INFORMATION: RNA
<220> FEATURE:
<221> NAME/KEY: misc_feature
<222> LOCATION: (21)..(21)
<223> OTHER INFORMATION: RNA
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 37
acgaaagccg atgactaaug c                                               21

<210> SEQ ID NO 38
<211> LENGTH: 21
<212> TYPE: DNA
<213> ORGANISM: Artificial Sequence
<220> FEATURE:
<223> OTHER INFORMATION: DNA/RNA PROBE
<220> FEATURE:
<221> NAME/KEY: misc_feature
<222> LOCATION: (1)..(1)
<223> OTHER INFORMATION: 5' TETRAMETHYLRHODAMINE
<220> FEATURE:
<221> NAME/KEY: misc_feature
<222> LOCATION: (1)..(1)
<223> OTHER INFORMATION: 2' FLUORO RNA
<220> FEATURE:
<221> NAME/KEY: misc_feature
<222> LOCATION: (7)..(7)
<223> OTHER INFORMATION: 2' FLUORO RNA
<220> FEATURE:
```

```
<221> NAME/KEY: misc_feature
<222> LOCATION: (11)..(11)
<223> OTHER INFORMATION: 2' FLUORO RNA
<220> FEATURE:
<221> NAME/KEY: misc_feature
<222> LOCATION: (15)..(15)
<223> OTHER INFORMATION: 2' FLUORO RNA
<220> FEATURE:
<221> NAME/KEY: misc_feature
<222> LOCATION: (19)..(19)
<223> OTHER INFORMATION: 2' FLUORO RNA
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 38
acgaaagccg atgactaaug c                                              21

<210> SEQ ID NO 39
<211> LENGTH: 21
<212> TYPE: DNA
<213> ORGANISM: Artificial Sequence
<220> FEATURE:
<223> OTHER INFORMATION: DNA/RNA PROBE
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (1)..(1)
<223> OTHER INFORMATION: 2' FLUORO RNA
<220> FEATURE:
<221> NAME/KEY: misc_feature
<222> LOCATION: (3)..(3)
<223> OTHER INFORMATION: 2' FLUORO RNA
<220> FEATURE:
<221> NAME/KEY: misc_feature
<222> LOCATION: (5)..(5)
<223> OTHER INFORMATION: 2' FLUORO RNA
<220> FEATURE:
<221> NAME/KEY: misc_feature
<222> LOCATION: (7)..(7)
<223> OTHER INFORMATION: 2' FLUORO RNA
<220> FEATURE:
<221> NAME/KEY: misc_feature
<222> LOCATION: (9)..(9)
<223> OTHER INFORMATION: 2' FLUORO RNA
<220> FEATURE:
<221> NAME/KEY: misc_feature
<222> LOCATION: (11)..(11)
<223> OTHER INFORMATION: 2' FLUORO RNA
<220> FEATURE:
<221> NAME/KEY: misc_feature
<222> LOCATION: (13)..(13)
<223> OTHER INFORMATION: 2' FLUORO RNA
<220> FEATURE:
<221> NAME/KEY: misc_feature
<222> LOCATION: (15)..(15)
<223> OTHER INFORMATION: 2' FLUORO RNA
<220> FEATURE:
<221> NAME/KEY: misc_feature
<222> LOCATION: (17)..(17)
<223> OTHER INFORMATION: 2' FLUORO RNA
<220> FEATURE:
<221> NAME/KEY: misc_feature
<222> LOCATION: (19)..(19)
<223> OTHER INFORMATION: 2' FLUORO RNA
<220> FEATURE:
<221> NAME/KEY: misc_feature
<222> LOCATION: (21)..(21)
<223> OTHER INFORMATION: 2' FLUORO RNA
<220> FEATURE:
<221> NAME/KEY: misc_feature
<222> LOCATION: (21)..(21)
<223> OTHER INFORMATION: 3' BLACK HOLE QUENCHER 2 TAG
```

<400> SEQUENCE: 39
acgaaagccg atgactaaug c                                              21

<210> SEQ ID NO 40
<211> LENGTH: 21
<212> TYPE: DNA
<213> ORGANISM: Artificial Sequence
<220> FEATURE:
<223> OTHER INFORMATION: DNA/RNA PROBE
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (1)..(3)
<223> OTHER INFORMATION: 2' FLUORO RNA
<220> FEATURE:
<221> NAME/KEY: misc_feature
<222> LOCATION: (5)..(7)
<223> OTHER INFORMATION: 2' FLUORO RNA
<220> FEATURE:
<221> NAME/KEY: misc_feature
<222> LOCATION: (9)..(11)
<223> OTHER INFORMATION: 2' FLUORO RNA
<220> FEATURE:
<221> NAME/KEY: misc_feature
<222> LOCATION: (13)..(15)
<223> OTHER INFORMATION: 2' FLUORO RNA
<220> FEATURE:
<221> NAME/KEY: misc_feature
<222> LOCATION: (17)..(19)
<223> OTHER INFORMATION: 2' FLUORO RNA
<220> FEATURE:
<221> NAME/KEY: misc_feature
<222> LOCATION: (21)..(21)
<223> OTHER INFORMATION: 2' FLUORO RNA
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 40
acgaaagccg atgactaaug c                                              21

<210> SEQ ID NO 41
<211> LENGTH: 21
<212> TYPE: DNA
<213> ORGANISM: Artificial Sequence
<220> FEATURE:
<223> OTHER INFORMATION: DNA/RNA PROBE
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (1)..(1)
<223> OTHER INFORMATION: 2' O METHYL RNA
<220> FEATURE:
<221> NAME/KEY: misc_feature
<222> LOCATION: (7)..(7)
<223> OTHER INFORMATION: 2' O METHYL RNA
<220> FEATURE:
<221> NAME/KEY: misc_feature
<222> LOCATION: (11)..(11)
<223> OTHER INFORMATION: 2' O METHYL RNA
<220> FEATURE:
<221> NAME/KEY: misc_feature
<222> LOCATION: (15)..(15)
<223> OTHER INFORMATION: 2' O METHYL RNA
<220> FEATURE:
<221> NAME/KEY: misc_feature
<222> LOCATION: (19)..(19)

```
<223> OTHER INFORMATION: 2' O METHYL RNA
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 41
acgaaagccg atgactaaug c                                              21

<210> SEQ ID NO 42
<211> LENGTH: 21
<212> TYPE: DNA
<213> ORGANISM: Artificial Sequence
<220> FEATURE:
<223> OTHER INFORMATION: RNA PROBE
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (1)..(1)
<223> OTHER INFORMATION: 2' O METHYL RNA
<220> FEATURE:
<221> NAME/KEY: misc_feature
<222> LOCATION: (3)..(3)
<223> OTHER INFORMATION: 2' O METHYL RNA
<220> FEATURE:
<221> NAME/KEY: misc_feature
<222> LOCATION: (5)..(5)
<223> OTHER INFORMATION: 2' O METHYL RNA
<220> FEATURE:
<221> NAME/KEY: misc_feature
<222> LOCATION: (7)..(7)
<223> OTHER INFORMATION: 2' O METHYL RNA
<220> FEATURE:
<221> NAME/KEY: misc_feature
<222> LOCATION: (9)..(9)
<223> OTHER INFORMATION: 2' O METHYL RNA
<220> FEATURE:
<221> NAME/KEY: misc_feature
<222> LOCATION: (11)..(11)
<223> OTHER INFORMATION: 2' O METHYL RNA
<220> FEATURE:
<221> NAME/KEY: misc_feature
<222> LOCATION: (13)..(13)
<223> OTHER INFORMATION: 2' O METHYL RNA
<220> FEATURE:
<221> NAME/KEY: misc_feature
<222> LOCATION: (15)..(15)
<223> OTHER INFORMATION: 2' O METHYL RNA
<220> FEATURE:
<221> NAME/KEY: misc_feature
<222> LOCATION: (17)..(17)
<223> OTHER INFORMATION: 2' O METHYL RNA
<220> FEATURE:
<221> NAME/KEY: misc_feature
<222> LOCATION: (19)..(19)
<223> OTHER INFORMATION: 2' O METHYL RNA
<220> FEATURE:
<221> NAME/KEY: misc_feature
<222> LOCATION: (21)..(21)
<223> OTHER INFORMATION: 2' O METHYL RNA
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 42
acgaaagccg atgactaaug c                                              21

<210> SEQ ID NO 43
<211> LENGTH: 21
<212> TYPE: DNA
<213> ORGANISM: Artificial Sequence
```

-continued

```
<220> FEATURE:
<223> OTHER INFORMATION: DNA/RNA PROBE
<220> FEATURE:
<221> NAME/KEY: misc_feature
<222> LOCATION: (1)..(1)
<223> OTHER INFORMATION: 5' TETRAMETHYLRHODAMINE TAG
<220> FEATURE:
<221> NAME/KEY: misc_feature
<222> LOCATION: (1)..(3)
<223> OTHER INFORMATION: 2' O METHYL RNA
<220> FEATURE:
<221> NAME/KEY: misc_feature
<222> LOCATION: (5)..(7)
<223> OTHER INFORMATION: 2' O METHYL RNA
<220> FEATURE:
<221> NAME/KEY: misc_feature
<222> LOCATION: (9)..(11)
<223> OTHER INFORMATION: 2' O METHYL RNA
<220> FEATURE:
<221> NAME/KEY: misc_feature
<222> LOCATION: (13)..(15)
<223> OTHER INFORMATION: 2' O METHYL RNA
<220> FEATURE:
<221> NAME/KEY: misc_feature
<222> LOCATION: (17)..(19)
<223> OTHER INFORMATION: 2' O METHYL RNA
<220> FEATURE:
<221> NAME/KEY: misc_feature
<222> LOCATION: (21)..(21)
<223> OTHER INFORMATION: 2' O METHYL RNA
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 43
acgaaagccg atgactaaug c                                           21

<210> SEQ ID NO 44
<211> LENGTH: 20
<212> TYPE: DNA
<213> ORGANISM: Artificial Sequence
<220> FEATURE:
<223> OTHER INFORMATION: TARGET DNA SEQUENCE

<400> SEQUENCE: 44
gatctcagta cacatcaact                                             20

<210> SEQ ID NO 45
<211> LENGTH: 21
<212> TYPE: DNA
<213> ORGANISM: Artificial Sequence
<220> FEATURE:
<223> OTHER INFORMATION: DNA/RNA PROBE
<220> FEATURE:
<221> NAME/KEY: misc_feature
<222> LOCATION: (1)..(1)
<223> OTHER INFORMATION: 5' CARBOYTETRAMETHYLRHODAMINE TAG
<220> FEATURE:
<221> NAME/KEY: misc_feature
<222> LOCATION: (7)..(7)
<223> OTHER INFORMATION: RNA BASE
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 45
acgaaagccg atgactaatg c                                           21

<210> SEQ ID NO 46
<211> LENGTH: 21
<212> TYPE: DNA
```

```
<213> ORGANISM: Artificial Sequence
<220> FEATURE:
<223> OTHER INFORMATION: DNA/RNA PROBE
<220> FEATURE:
<221> NAME/KEY: misc_feature
<222> LOCATION: (1)..(1)
<223> OTHER INFORMATION: 56-TAMN TAG
<220> FEATURE:
<221> NAME/KEY: misc_feature
<222> LOCATION: (7)..(7)
<223> OTHER INFORMATION: RNA BASE
<220> FEATURE:
<221> NAME/KEY: misc_feature
<222> LOCATION: (19)..(19)
<223> OTHER INFORMATION: RNA BASE
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 46
acgaaagccg atgactaaug c                                      21

<210> SEQ ID NO 47
<211> LENGTH: 21
<212> TYPE: DNA
<213> ORGANISM: Artificial Sequence
<220> FEATURE:
<223> OTHER INFORMATION: DNA/RNA PROBE
<220> FEATURE:
<221> NAME/KEY: misc_feature
<222> LOCATION: (1)..(1)
<223> OTHER INFORMATION: 5' CARBOXYTETRAMETHYLRHODAMINE TAG
<220> FEATURE:
<221> NAME/KEY: misc_feature
<222> LOCATION: (7)..(7)
<223> OTHER INFORMATION: RNA BASE
<220> FEATURE:
<221> NAME/KEY: misc_feature
<222> LOCATION: (15)..(15)
<223> OTHER INFORMATION: RNA BASE
<220> FEATURE:
<221> NAME/KEY: misc_feature
<222> LOCATION: (19)..(19)
<223> OTHER INFORMATION: RNA BASE
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 47
acgaaagccg atgactaaug c                                      21

<210> SEQ ID NO 48
<211> LENGTH: 21
<212> TYPE: DNA
<213> ORGANISM: Artificial Sequence
<220> FEATURE:
<223> OTHER INFORMATION: DNA/RNA PROBE
<220> FEATURE:
<221> NAME/KEY: misc_feature
<222> LOCATION: (1)..(1)
<223> OTHER INFORMATION: 5' CARBOXYTETRAMETHYLRHODAMINE TAG
<220> FEATURE:
<221> NAME/KEY: misc_feature
<222> LOCATION: (1)..(1)
<223> OTHER INFORMATION: RNA BASE
<220> FEATURE:
<221> NAME/KEY: misc_feature
<222> LOCATION: (7)..(7)
<223> OTHER INFORMATION: RNA BASE
<220> FEATURE:
<221> NAME/KEY: misc_feature
<222> LOCATION: (15)..(15)
<223> OTHER INFORMATION: RNA BASE
```

```
<220> FEATURE:
<221> NAME/KEY: misc_feature
<222> LOCATION: (19)..(19)
<223> OTHER INFORMATION: RNA BASE
<220> FEATURE:
<221> NAME/KEY: misc_feature
<222> LOCATION: (21)..(21)
<223> OTHER INFORMATION: 3' BLACK HOLE QUENCHER 2 TAG

<400> SEQUENCE: 48
acgaaagccg atgactaaug c                                              21
```

DETECTION OF NUCLEIC ACIDS BY STRAND INVASION BASED AMPLIFICATION

CROSS REFERENCE TO RELATED APPLICATIONS

This application is a national phase application under 35 U.S.C. § 371 that claims priority to International Application No. PCT/EP2014/075321 filed Nov. 21, 2014, which claims priority to European Patent Application No. 13194118.9 filed Nov. 22, 2013, all of which are incorporated herein by reference in their entirety.

FIELD OF THE INVENTION

The invention relates to a method for detection of a target nucleic acid sequence in a sample in the presence of at least one protein capable of binding to single-stranded DNA, wherein an oligonucleotide probe comprising a fluorophore, a quencher and a region complementary to the target nucleic acid sequence is used for detection. The sequence of the oligonucleotide probe comprises at least 20% RNA nucleotides, modified RNA nucleotides and/or PNA nucleotides. The invention also relates to oligonucleotide probes, compositions and kits suitable for use in this method, and their use for diagnosis of an infection by a pathogen.

BACKGROUND TO THE INVENTION

Detection of target nucleic acid sequences has been performed using DNA probes comprising fluorophore/quencher pairs. Such probes exhibit a change in quenching activity on binding to a target nucleic acid, allowing for quantitative detection of target. Probes can be used to monitor DNA amplification in real time, and different targets may be detected in the same reaction through use of different fluorophore/quencher pairs on each probe for the targets to be detected, thus allowing multiplexing. Examples of previous probe systems for detection of DNA amplification include hybridisation probes showing conformational changes on target binding (U.S. Pat. No. 7,241,596), molecular beacons (U.S. Pat. No. 5,925,517), Taqman chemistry (U.S. Pat. No. 6,214,979), and endonuclease-cleavable probes (U.S. Pat. No. 7,435,561 and US20050214809). An isothermal DNA amplification process relying on an upstream primer, a downstream primer, and a strand invasion system is described in WO 2009/150467.

SUMMARY OF THE INVENTION

The present invention is based in part on the recognition of a problem associated with use of DNA probes in detection assays where proteins capable of binding to single-stranded DNA are present. The present inventors found that DNA probes were unable to provide for a specific, template-dependent signal in the presence of proteins capable of binding to single-stranded DNA, and indeed gave a signal even in absence of template. This problem led them to investigate a solution that could provide for reliable template-dependent detection of DNA amplification in the context of proteins capable of binding to single-stranded DNA. The inventors surprisingly discovered that the incorporation of RNA nucleotides, modified RNA nucleotides and/or Peptide Nucleic acid (PNA) nucleotides into the sequence of an oligonucleotide probe labeled with a fluorophore and a quencher provided resistance to disruption of fluorescent signal by proteins capable of binding to single-stranded DNA as compared to a corresponding fully DNA probe.

The present invention provides a method for detection of a target nucleic acid sequence in a sample in the presence of at least one protein capable of binding to single-stranded DNA comprising contacting said sample with at least one oligonucleotide probe comprising a fluorophore, a quencher and a region complementary to said target nucleic acid sequence, wherein the sequence of said oligonucleotide probe comprises at least 20% RNA nucleotides, modified RNA nucleotides and/or PNA nucleotides.

The invention further provides an oligonucleotide probe comprising a fluorophore, a quencher and a region complementary to a target nucleic acid sequence, wherein the sequence of said oligonucleotide probe comprises at least 20% RNA nucleotides, modified RNA nucleotides and/or PNA nucleotides. The invention additionally provides a composition and a kit, each comprising an oligonucleotide probe of the invention, and in addition a strand invasion oligonucleotide comprising a region complementary to said target nucleic acid sequence and/or at least one protein capable of binding to single-stranded DNA. The invention also provides a method for diagnosis of a disease in a subject, comprising carrying out a method for detection of a nucleic acid sequence of the invention in a sample from a subject to detect a target nucleic acid sequence associated with said disease.

DESCRIPTION OF THE SEQUENCES

Figure 1A:
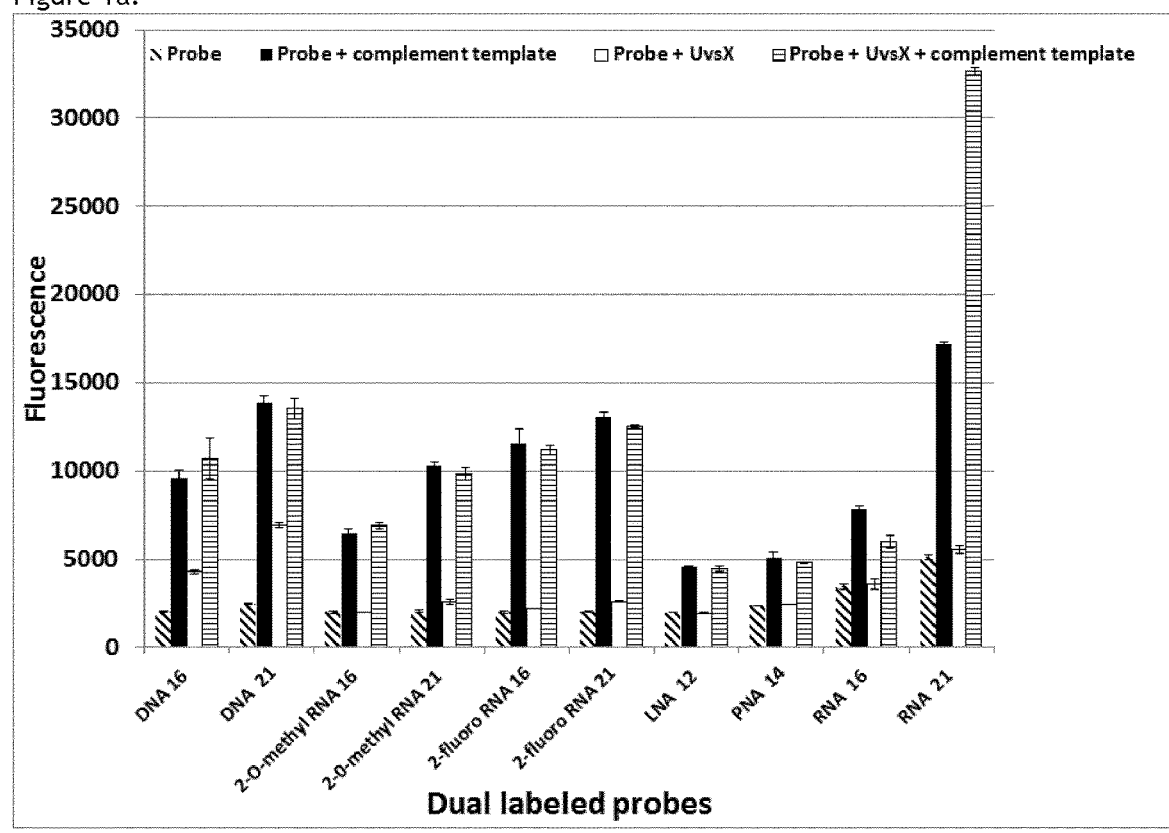
FIG. 1 shows the effect of (A) a recombinase (UvsX), (B) a single strand DNA binding protein (gp32), (C) a reagent mixture for strand invasion based amplification, D) the *E. coli* recombinase RecA, and E) the single stranded DNA binding protein ET-SSB on signal from probes containing a fluorophore and quencher. X-axis for (A) and (B): left to right—four conditions for each tested probe (probe only; probe with complementary template; probe with protein(s); probe with protein(s) and complementary template). X axis for (C): left to right—two conditions for each tested probe (probe and reagent composition; probe, reagent composition and complementary template). X axis for (D) and (E)): left to right—two conditions for each tested probe (probe only, probe with protein). Tested probes were DNA 16 (SEQ ID NO:1), DNA 21 (SEQ ID NO:2), 2'-O-methyl RNA 16 (SEQ ID NO: 5), 2'-O-methyl RNA 21 (SEQ ID NO: 6), 2'-fluoro RNA 16 (SEQ ID NO:7), 2'-fluoro RNA 21 (SEQ ID NO: 8), LNA 12 (SEQ ID NO: 9), PNA 14 (SEQ ID NO: 10), RNA 16 (SEQ ID NO: 3) and RNA 21 (SEQ ID NO: 4). Y-axis for each chart: fluorescence (arbitrary units).

SEQ ID NO:1 is the nucleotide sequence of a DNA probe.
SEQ ID NO:2 is the nucleotide sequence of a DNA probe.
SEQ ID NO:3 is the nucleotide sequence of an RNA probe.
SEQ ID NO:4 is the nucleotide sequence of an RNA probe.
SEQ ID NO:5 is the nucleotide sequence of a 2'-O-methyl RNA probe.
SEQ ID NO:6 is the nucleotide sequence of a 2'-O-methyl RNA probe
SEQ ID NO:7 is the nucleotide sequence of a 2'-fluoro RNA probe
SEQ ID NO:8 is the nucleotide sequence of a 2'-fluoro RNA probe
SEQ ID NO:9 is the nucleotide sequence of an LNA probe.
SEQ ID NO:10 is the sequence of a PNA probe.
SEQ ID NO:11 is the nucleotide sequence of a DNA primer.
SEQ ID NO:12 is the nucleotide sequence of a DNA primer.
SEQ ID NO:13 is the nucleotide sequence of a 2'-fluoro RNA primer.
SEQ ID NO:14 is the nucleotide sequence of a mixed DNA/2'-fluoro RNA primer.
SEQ ID NO:15 is the nucleotide sequence of a DNA strand invasion oligonucleotide.
SEQ ID NO:16 is the nucleotide sequence of a DNA probe.
SEQ ID NO:17 is the nucleotide sequence of a 2'-fluoro RNA probe.
SEQ ID NO:18 is the nucleotide sequence of an LNA probe.
SEQ ID NO:19 is the sequence of a mixed DNA/2'-fluoro RNA probe/primer.
SEQ ID NO:20 is the nucleotide sequence of an artificial DNA target nucleic acid sequence.
SEQ ID NO:21 is the nucleotide sequence of a DNA primer.

SEQ ID NO:22 is the nucleotide sequence of a DNA primer.

SEQ ID NO:23 is the nucleotide sequence of a DNA strand invasion oligonucleotide.

SEQ ID NO:24 is the nucleotide sequence of a 2'-fluoro RNA probe.

SEQ ID NO:25 is the nucleotide sequence of a 2'-fluoro RNA probe.

SEQ ID NO:26 is a target DNA nucleotide sequence from *C. difficile* ATCC BAA 1382

SEQ ID NO:27 is the nucleotide sequence of a DNA primer.

SEQ ID NO:28 is the nucleotide sequence of a DNA primer.

SEQ ID NO:29 is the nucleotide sequence of a DNA strand invasion oligonucleotide.

SEQ ID NO:30 is the nucleotide sequence of a 2'-fluoro RNA probe.

SEQ ID NO:31 is a target DNA nucleotide sequence from *S. typhimurium* ATCC 14028

SEQ ID NO:32 is the nucleotide sequence of a 2'-O-methyl RNA probe.

SEQ ID NO:33 is the nucleotide sequence of a DNA primer.

SEQ ID NO:34 is a complementary target DNA nucleotide sequence for the probes of SEQ ID NOs 1 to 8.

SEQ ID NOs: 35 to 43 represent the nucleotide sequences of chimeric DNA/RNA, DNA/2'-fluoro RNA and DNA/2'-O-methyl RNA probes.

SEQ ID NO:44 is a complementary target DNA nucleotide sequence for the probes of SEQ ID NOs 9 and 10.

SEQ ID NOs:45 to 48 represent the nucleotide sequences of chimeric DNA/RNA probes.

DETAILED DESCRIPTION OF THE INVENTION

It is to be understood that different applications of the disclosed methods may be tailored to the specific needs in the art. It is also to be understood that the terminology used herein is for the purpose of describing particular embodiments of the invention only, and is not intended to be limiting. In addition as used in this specification and the appended claims, the singular forms "a", "an", and "the" include plural referents unless the content clearly dictates otherwise. Thus, for example, reference to "an oligonucleotide" includes two or more such oligonucleotides, and the like. All publications, patents and patent applications cited herein, whether supra or infra, are hereby incorporated by reference in their entirety.

Method for Detection of a Target Nucleic Acid Sequence

Sample

Any sample may be used for detection of the target nucleic acid sequence, provided that nucleic acid can be obtained or derived from the sample. The sample may be for instance an environmental sample, a reference sample or a clinical sample. Where the methods of the invention are used for diagnosis of a disease by detection of a target nucleic acid sequence, the sample is commonly a clinical sample, for example a sample obtained from a patient suspected of having, or having the disease. Suitable types of clinical sample vary according to the particular type of disease or infection that is present, or suspected of being present in a subject. The sample may be a saliva, sputum, blood, plasma, serum, urine or stool sample. The sample may be a cell or tissue sample. In preferred embodiments, the samples are taken from animal subjects, such as mammalian subjects. The samples will commonly be taken from human subjects, but the present invention is also applicable in general to domestic animals, livestock, birds and fish. For example, the invention may be applied in a veterinary or agricultural setting. In embodiments where the invention detects infection of an infection by *Clostridium difficile* (*C. difficile*) or *Salmonella typhimurium* (*S. typhimurium*) the sample is preferably a stool sample. The stool sample may be taken from a subject having a gastrointestinal tract infection. The infection may be present in a patient having diarrhoea.

The sample comprises nucleic acid which may be DNA or RNA. If the nucleic acid is present in the sample in a suitable form allowing for detection according to the invention, the sample may be used directly. However, typically, nucleic acid is derived, obtained or extracted from the sample. Methods for processing samples containing nucleic acids, extracting nucleic acids and/or purifying nucleic acids for use in detection methods are well-known in the art. Total nucleic acid may be isolated or DNA and RNA may be isolated separately.

Typically, a sample is processed in an appropriate manner such that nucleic acid is provided in a convenient form for contacting with the oligonucleotide probe and single-stranded DNA binding protein and optional further nucleic acid components. Where the nucleic acid is DNA, the DNA is typically provided in double-stranded form. Where the nucleic acid is an RNA, it is typically converted to cDNA using reverse transcriptase or a polymerase with reverse transcriptase activity. RNA may be useful for bacterial detection, owing to the very large number of ribosomes present in bacterial cells which effectively amplify the concentration of target sequences. In addition to ribosomal RNA (rRNA), other forms of RNA, for examples transfer RNAs (tRNA), messenger RNAs (mRNA), small interfering RNAs (siRNA), small nuclear ribonucleic acid (snRNA), microRNAs (miRNA) may also be useful for prokaryote and eukaryote detection.

Target Nucleic Acid Sequence

Any target nucleic acid sequence of any origin may be detected. The target nucleic acid sequence may be human, mammalian, bacterial or viral. The target nucleic acid sequence may be a region of a gene or chromosome. Preferably, the target nucleic acid sequence is specific for the genotype or the organism (such as the pathogen) to be detected. The target nucleic acid sequence may be unique to the genome of a particular species. Thus, the target nucleic acid sequence for detecting a particular species will typically differ from any homologous nucleic acid sequence in a related species. Typically, the target nucleic acid sequence will comprise several mismatches with a homologous nucleic acid sequence in a related species. The target nucleic acid sequence may be a sequence specific to a particular strain of bacteria or a particular serotype, isolate or clade of a virus. The target nucleic acid sequence may be specific for a toxigenic strain of *C. difficile* or for a strain of *S. typhimurium*.

The target nucleic acid sequence to be detected may be of any size and have any sequence. The target nucleic acid sequence comprises a region complementary to the oligonucleotide probe. Typically, the target nucleic acid sequence is amplified in conjunction with detection by the probe and thus comprises further regions which are complementary to primers. Where a target nucleic acid sequence (or amplicon) is amplified by strand-invasion based amplification under isothermal conditions, it typically has a sufficient length to provide for specific detection of the target genotype or organism and for hybridisation of the upstream and downstream primers and strand invasion oligonucleotide in a suitable manner. Preferably, an amplicon for strand-invasion based DNA amplification under isothermal conditions is at least 45 nucleotides in length, more preferably at least 50, at least 55 or at least 60 nucleotides in length, as measured from the 5' site of binding of the upstream primer to the 5' site of binding of the downstream primer.

An example of a suitable target nucleic acid sequence for detection of toxigenic *C. difficile* is SEQ ID NO 26. An example of a suitable target sequence for detection of *S. typhimurium* is SEQ ID NO 31.

More than one target nucleic acid sequence may be detected in a method of the invention by providing two or more oligonucleotide probes each specific for a different target nucleic acid sequence. Typically, the oligonucleotide probes binding to different target nucleic acid sequences will be labeled with different fluorophore/quencher pairs, thus allowing for multiplexing. At least two, three, four, five, ten or more different target sequences may be detected. More than one target nucleic acid sequence from the same organism may be detected. Alternatively, target nucleic acid sequences specific for at least two, three, four, five, ten or more different genotypes, organisms or pathogens may be detected.

Oligonucleotide Probe

The oligonucleotide probe comprises a region complementary to the target nucleic acid sequence, a fluorophore and a quencher. The sequence of the oligonucleotide probe comprises at least 20% RNA nucleotides, modified RNA nucleotides and/or PNA nucleotides. In other words, at least 20% of the nucleotides present in the oligonucleotide probe are RNA nucleotides, modified RNA nucleotides and/or PNA nucleotides. The oligonucleotide may comprise a mixture of RNA nucleotides, modified RNA nucleotides and/or PNA nucleotides, such as a mixture of RNA nucleotides and modified RNA nucleotides. Alternatively, the sequence of the oligonucleotide probe may comprise DNA nucleotides and at least 20% RNA nucleotides, DNA nucleotides and at least 20% modified RNA nucleotides, or DNA nucleotides and at least 20% PNA nucleotides.

More preferably, the sequence of the oligonucleotide probe comprises at least 25%, at least 30%, at least 35%, at least 40%, at least 50%, at least 60%, at least 70%, at least 80%, or at least 90% RNA nucleotides, modified RNA nucleotides and/or PNA nucleotides.

Where the oligonucleotide probe is of 12 to 25 or 15 to 25 nucleotides in length, the oligonucleotide probe typically comprises at least 5 RNA nucleotides, modified RNA nucleotides and/or PNA nucleotides, more preferably at least 6, at least 7, at least 8, at least 9, or at least 10 RNA nucleotides, modified RNA nucleotides and/or PNA nucleotides. An oligonucleotide probe of up to 20 nucleotides in length (such as 10 to 20 or 12 to 20 nucleotides in length) typically comprises at least 4 RNA nucleotides, modified RNA nucleotides and/or PNA nucleotides, more preferably at least 6, at least 7, at least 8, at least 9, or at least 10 RNA nucleotides, modified RNA nucleotides and/or PNA nucleotides. An oligonucleotide probe of 20 to 25 nucleotides in length may comprise at least 12, at least 15, or at least 18 RNA nucleotides, modified RNA nucleotides and/or PNA nucleotides. An oligonucleotide probe of 8 to 12 nucleotides in length may comprise at least 3, at least 4, or at least 6 RNA nucleotides, modified RNA nucleotides and/or PNA nucleotides. The sequence of the oligonucleotide probe comprises sufficient RNA nucleotides, modified RNA nucleotides and/or PNA nucleotides to prevent a fluorescent signal from the probe in the presence of a protein capable of binding to single-stranded DNA in the absence of a complementary template sequence.

In particularly preferred embodiments, the nucleotide sequence of the oligonucleotide probe is composed solely of ribonucleotides (which may be natural ribonucleotides or modified ribonucleotides) or solely of PNA nucleotides. The nucleotide sequence of the probe may be composed solely of natural ribonucleotides, solely of modified ribonucleotides, or of a mixture of natural and modified ribonucleotides. The oligonucleotide probe may have a mixed backbone of RNA nucleotides and PNA nucleotides or modified RNA nucleotides and PNA nucleotides. Preferred modified ribonucleotides include 2'-fluoro ribonucleotides, 2'-O-methyl ribonucleotides, and LNA (locked nucleic acid) nucleotides, and combinations thereof. Any of the above percentage contents or minimum numbers for modified RNA nucleotides may apply specifically to the proportion of 2'-fluoro ribonucleotides, 2'-O-methyl ribonucleotides, or LNA nucleotides in the probe. Alternatively, the probe may be composed solely of 2'-fluoro ribonucleotides, 2'-O-methyl ribonucleotides, or LNA nucleotides. Other suitable modified ribonucleotides include 2'-O-methoxy-ethyl and other 2'-substitutions.

In some embodiments, provided that the oligonucleotide probe comprises at least 20% RNA nucleotides, modified RNA nucleotides and/or PNA nucleotides, it may further comprise deoxyribonucleotides, which may be natural deoxyribonucleotides or modified deoxyribonucleotides. Where the oligonucleotide probe is of 25 nucleotides in length or less, it typically comprises less than 20, more preferably less than 18, less than 15, less than 12, or less than 10 deoxyribonucleotides. The oligonucleotide probe may comprise 1 to 5, 1 to 8, 1 to 10, or 1 to 15 deoxyribonucleotides. Where the oligonucleotide probe comprises deoxyribonucleotides or modified deoxyribonucleotides, these may be present at the 5' and/or 3'end of a sequence of ribonucleotides or modified ribonucleotides. The oligonucleotide probe may for example comprise 1, 2, 3, 4 or 5 deoxyribonucleotides or modified deoxyribonucleotides at its 5' end and/or 3'end. Alternatively, the deoxyribonucleotides or modified deoxyribonucleotides may be interspersed in a sequence of ribonucleotides.

The oligonucleotide probe is typically about 8 to about 25 nucleotides in length. The probe is typically at least 8 nucleotides in length or less than 30 nucleotides in length, more preferably less than 25 nucleotides in length. The probe may be at least 10, at least 12, or at least 15 nucleotides in length. The probe may be about 10 to about 20, about 12 to about 25, about 15 to about 25, or about 12 to about 22 nucleotides in length. The length of the probe is selected according to the requirement for specific or selective hybridisation with a region of the target sequence under the conditions used, and may be selected based on the length of primers used for amplification of the target sequence, as discussed below.

Specific or selective hybridisation refers to the binding of an oligonucleotide (for example a probe or primer) only to a particular nucleotide sequence under given conditions, when that sequence is present in a nucleic acid in a sample, such as a complex biological mixture including total cellular and foreign DNA or RNA. Appropriate hybridisation conditions are known in the art. See for example, Sambrook, Fritsche and Maniatis "Molecular Cloning: A Laboratory Manual", 2nd Ed. Cold Spring Harbor Press (1989), which is hereby incorporated by reference in its entirety. Appropriate hybridisation conditions are also provided in the Examples below. As is known to the skilled person, appropriate hybridisation conditions may vary depending on the length of a probe and its base composition. Hybridisation is typically performed at the same temperature as amplification, and thus also depends on the activity profile of the enzymes used for amplification, including the polymerase and the recombinase as applicable depending on the method of amplification.

The nucleotide sequence of the probe may be partly or full complementary to a region of the target nucleic acid sequence. An oligonucleotide probe of less than 25 nucleotides in length will typically comprise a region of at least 10, at least 15 or at least 20 nucleotides in length which is complementary to a region of the target nucleic acid sequence. The oligonucleotide probe may further comprise flanking regions of 1, 2, 3, 4, 5, 8 or 10 nucleotides in length 5' or 3' to the complementary region which are not complementary to the target nucleic acid sequence. The oligonucleotide probe may comprise a total of 1, 2, 3, 4, or 5, 8 or 10 nucleotides at the 5' and 3' ends flanking the complementary sequence, which are not complementary to the target nucleic acid sequence. Such flanking regions may be self-complementary, leading to a hairpin structure.

Mismatches may be present between the oligonucleotide probe and the target nucleic acid sequence while still allowing for specific detection of the target nucleic acid sequence, in particular where the target nucleic acid sequence is amplified using upstream and downstream primers specific for the target sequence. The binding of the probe in combination with specific amplification will specifically detect the target sequence. There may be 1, 2, 3, 4 or 5 mismatches between the complementary region of the oligonucleotide probe and the corresponding region of the target nucleic acid sequence. Any mismatches in the probe sequence are preferably at least 4, at least 5, at least 8 or at least ten nucleotides apart.

Preferably, the probe is though fully complementary to a region of the target nucleic acid sequence.

The oligonucleotide probe may have a region of secondary structure whose conformation is altered on binding to the target nucleic acid sequence. Thus, the oligonucleotide probe may comprise a hairpin stem formed by self-complementary regions at the 5' and 3' ends of the probe, and a loop region comprising the region of complementarity to the target sequence. In such an embodiment, the fluorophore and quencher are typically located at the 5' and 3' ends of the probe, in close proximity to each other in the stem region, such that fluorescence is quenched in the absence of the target nucleic acid sequence. The oligonucleotide probe may be a molecular beacon probe. In other embodiments, the oligonucleotide probe does not have any region of secondary structure or is not a molecular beacon probe.

The oligonucleotide probe may have both a probe and a primer function. Thus, the oligonucleotide probe may be capable or priming amplification of its target nucleic acid sequence. An oligonucleotide probe acting as a primer may be composed solely of RNA, modified RNA or PNA. Alternatively, an oligonucleotide probe acting as a primer may comprise 1 to 5, 1 to 8, 1 to 10, or 1 to 15 deoxyribonucleotides. An oligonucleotide probe acting as a primer may comprise at least one deoxyribonucleotide at its 3'end, more preferably, at least two, or at least three deoxyribonucleotides at its 3'end. The oligonucleotide probe may be an upstream or a downstream primer for its target nucleic acid sequence. An oligonucleotide probe which has a primer function will have a free 3'end and comprise one or both of the fluorophore and quencher at internal positions in the probe sequence. An oligonucleotide probe which has a primer function may have a fluorophore at the 5'end and a quencher at an internal position, or a quencher at the 3'end and a fluorophore at an internal position. The use of an oligonucleotide probe of the invention as a primer is described in more detail below.

The oligonucleotide probe may be labeled with any fluorophore and any quencher. The fluorophore and quencher will be selected such that the absorption spectrum of the quencher overlaps with the emission spectrum of the fluorophore. The fluorophore and quencher will further be selected and positioned in the probe such that, upon hybridization with a target template, the fluorophore produces an increase in signal due to reduced quenching effect.

The quencher may be non-fluorescent, for example a non-fluorescent chromophore. The quencher may be a dark quencher. Alternatively, the quencher may fluoresce with a different emission spectrum to the fluorophore, such that when specifically monitoring fluorescence of the fluorophore or the quencher, a change in either signal may report on hybridisation to the target template. The fluorophore and quencher are preferably positioned at the 5' and 3' termini of the probes, in particular in embodiments where polymerase-dependent extension of the probe is undesirable. The fluorophore may be located at the 5' terminus and the quencher at the 3' terminus of the probe. Alternatively, the quencher may be located at the 5' terminus and the fluorophore at the 3' terminus of the probe. The fluorophore and/or the quencher may also be located at internal positions within the probe, such as ten or less nucleotides away from the 5' or 3' terminus of the probe. For example, in a probe of less than 25 nucleotides in length the fluorophore or quencher may be located 1 to 3, 1 to 5, 1 to 8 or 1 to 10 nucleotides away from the 5' or 3' terminus of the probe. Preferably, only one of the fluorophore and the quencher is at an internal position, with the other member of the pair at the 5' or 3' terminus.

The fluorophore and quencher are typically positioned at least eight nucleotides apart in the sequence of the probe, more preferably at least ten, or at least twelve nucleotides apart, depending on the length of the probe. Where the probe is 15 to 25 nucleotides in length, the fluorophore and quencher may be at least eight, at least ten, at least twelve, at least fifteen or at least twenty nucleotides apart. The fluorophore and quencher may be located at the 5' and 3' termini, and thus the maximum distance apart that is possible in the probe. The distance between the fluorophore and quencher will be selected such that when the probe is hybridised to the target nucleic acid sequence (in an open or linear conformation) there will be reduced quenching of the fluorophore by the quencher, leading to a detectable signal for the presence of the target nucleic acid sequence. An appropriate distance between the fluorophore and quencher may be optimised empirically.

The fluorophore may be any fluorescent moiety, typically a fluorescent organic dye. The quencher may be any moiety which quenches the fluorescence of the fluorophore, and is typically a chromogenic molecule, such as an organic dye. The skilled person is able to select appropriate fluorophore-quencher pairs for an oligonucleotide probe based on their common general knowledge. Suitable pairings are discussed for example in the following references: Marras S E: Selection of Fluorophore and Quencher Pairs for Fluorescent Nucleic Acid Hybridization Probes. In: Fluorescent Energy Transfer Nucleic Acid Probes. Edited by Didenko V, vol. 335: Humana Press; 2006: 3-16, and Didenko V V: DNA probes using fluorescence resonance energy transfer (FRET): designs and applications. Biotechniques 2001, 31(5):1106-1116, 1118, 1120-1101.

Suitable fluorophores include, but are not limited to, fluorescein and fluorescein derivatives, such as carboxyfluoresceins (FAM, including 6-FAM, 5-FAM, dT FAM), VIC, hexachloro-6-carboxyfluorescein (HEX), and JOE, 5-(2'-aminoethyl)aminonaphthalene-1-sulphonic acid (EDANS), coumarin and coumarin derivatives such as 3-phenyl-7-isocyanatocoumarin, Lucifer yellow, NED, Texas red, tetramethylrhodamine, carboxytetramethylrhodamine (TAMRA), 6-carboxy-X-rhodamine (ROX), 5 carboxyrhodamine, N-(p-2-benzoxazolyl)phenyl)maleimide, cyanine dyes such as CY5, rhodamine dyes, xanthene dyes, naphthlyamines, acridines, benzoxadiazoles, stilbenes, and pyrenes. Suitable quenchers include, but are not limited to, DABSYL, 4'-(4-dimethylaminophenylazo)benzoic acid (DABCYL), 4-dimethylaminophenylazophenyl-4'-maleimide (DABMI), tetramethylrhodamine, carboxytetramethylrhodamine (TAMRA), Black Hole Quencher 1, Black Hole Quencher 2, Dark Quencher 1, Dark Quencher 2, Iowa Black RQ, Iowa Black FQ.

Preferred fluorophore/quencher pairings include:
TAMRA and Black Hole Quencher 2;
ROX and Black Hole Quencher 2;
ROX and DABCYL;
FAM (such as dT-FAM) and Iowa Black FQ;
FAM (such as dT-FAM) and DABCYL;
ROX and Iowa Black FQ;
CY5 and Iowa Black RQ.

The fluorophore and quencher are typically covalently attached to the probe. The fluorophore and quencher may be attached by any suitable linker to one or more nucleotides present in the sequence of the probe. The skilled person is able to select any appropriate linker based on their common general knowledge. Suitable linkers are discussed for example in Agrawal S (ed.): Protocols for Oligonucleotides and Analogs: Synthesis and Properties: Humana Press; 1993.

Particular oligonucleotide probes provided herein are complementary to nucleic acid target sequences in toxigenic *C. difficile* and *S. typhimurium*. Preferred examples of such probes are SEQ ID NOs 24 and 25 for toxigenic *C. difficile* and SEQ ID NO: 30 for *S. typhimurium*. The invention also provides the probes and probe-primers of SEQ ID NOs 3 to 10, 17 to 19, 32, 35 to 43 and 48.

Variants of SEQ ID NOs 3 to 10, 17 to 19, 24, 25, 30, 32, 35 to 43 and 48 are also provided as part of the present invention. Variants of 3 to 10, 17 to 19, 24, 25, 30, 32, 35 to 43 and 48 include probes which have a corresponding nucleotide sequence to that of the original probe but which comprise an alternative fluorophore and/or quencher. The above variants may comprise any appropriate fluorophore-quencher pair from the fluorophores and quenchers described herein.

Variants of SEQ ID NOs 3 to 10, 17 to 19, 24, 25, 30, 32, 35 to 43 and 48 may also have a corresponding nucleotide sequence to that of the original probe composed of a different pattern of natural ribonucleotides, modified ribonucleotides or PNA nucleotides. For example, the original probes of SEQ ID NOs 24, 25 and 30 are composed of 2'-fluoro ribonucleotides. The nucleotide sequence of variants thereof may comprise or be composed solely of natural ribonucleotides. Additional variants thereof may comprise alternative modified ribonucleotides in place of 2'-fluoro ribonucleotides, or a mixture of natural and modified ribonucleotides. Preferred alternative modified ribonucleotides include 2'-O-methyl ribonucleotides, and LNA (locked nucleic acid) nucleotides. Thus, for example variants of SEQ ID NOs 24, 25 and 30 may be composed of 2'-fluoro ribonucleotides and 1 to 8, 1 to 5 or 1 to 3 natural ribonucleotides, or 2'-fluoro ribonucleotides and 1 to 8, 1 to 5 or 1 to 3 2'-O-methyl ribonucleotides. Variants of SEQ ID NOs 24, 25 and 30 may comprise at least 20% of the corresponding LNA or PNA nucleotides, or be composed solely of corresponding LNA and PNA nucleotides.

Variant probes may also be chimeric probes which comprise 1 to 10, 1 to 5 or 1 to 3 deoxyribonucleotides or modified deoxyribonucleotides in place of corresponding ribonucleotides or PNA nucleotides in the sequence of SEQ ID NOs 3 to 10, 17 to 19, 24, 25, 30, 32 and 35 to 43. The invention also provides a variant of the DNA probe of SEQ ID NO: 16 which comprises at least 20% RNA nucleotides, modified RNA nucleotides and/or PNA nucleotides.

Variants of SEQ ID NOs 3 to 10, 17 to 19, 24, 25, 30, 32, 35 to 43 and 48 may also be oligonucleotides of less than 25 nucleotides in length comprising a region which is partly or fully complementary to at least eight contiguous nucleotides of the corresponding original probe sequence. Preferably, said variants will comprise a region which is partly or fully complementary to at least nine, at least ten, at least twelve or at least fourteen contiguous nucleotides of the corresponding original probe sequence. The above variants may comprise a region which has 1, 2, 3, 4 or 5 mismatches (substitutions) with respect to the corresponding region of the original probe sequence (and thus the target sequence) and thus is partly complementary thereto. Thus, for instance, the variants may comprise a region of at least twelve nucleotides in length which has 1, 2, or 3 mismatches to a corresponding region of at least twelve nucleotides of the original probe sequence. Any mismatches are preferably at least 4, at least 5, or at least 8 nucleotides apart.

Variants of SEQ ID NOs 3 to 10, 17 to 19, 24, 25, 30 and 32 may also be oligonucleotides of less than 25 nucleotides in length which have at least 70% sequence identity to the sequence of the corresponding original probe sequence, preferably at least 75%, at least 80%, more preferably at least 85%, at least 90%, or at least 95% sequence identity.

The above variant probes may comprise 5' and/or 3' flanking regions to the region which is partly or fully complementary to the original probe. The 5' and/or 3' flanking regions may comprise sequence which is non-complementary to the target nucleic acid sequence, or sequence complementary to the regions that flank the binding region of the original probe in the target nucleotide sequence. For example, in variants of SEQ ID NOs 24, 25 and 30, the 5' flanking region may comprise a sequence of 1-10, or 1-5 nucleotides in length which is complementary to the 1-10 or 1-5 nucleotides which are 5' to the binding region of the probe in the relevant target nucleic acid sequence of SEQ ID NO:26 or SEQ ID NO:31.

Detection of a Signal

The detection of the signal from the probe may be performed by any suitable means for detection of fluorescence. The probe may be used to detect the target nucleic acid sequence without any prior DNA amplification. More typically, the probe is used to detect the target nucleic acid sequence after or during amplification of the target nucleic acid sequence. Preferably, the signal from the probe is monitored in real time in conjunction with amplification of the target nucleic acid sequence.

A single signal from one probe for a single target sequence may be detected. Alternatively, probes detecting different target sequences may be used which each signal at different fluorescent wavelengths to provide for multiplex detection. Two or more, such as three, four, five, six, eight, ten or more different probes may be used for multiplex detection of several different target sequences in a single reaction.

Dyes which intercalate with amplified DNA may also be used in parallel with the oligonucleotide probe(s) to detect the amplification of DNA, such as SYBR green and thiazole orange.

DNA oligonucleotide probes for the same or alternative target sequences may also be used in parallel with the oligonucleotide probe(s).

The invention also provides for means to enhance signal from the probe. The sample in which detection of the target nucleic acid sequence is to be performed may be contacted with an RNase H enzyme, such as RNase H2. A preferred RNase H2 enzyme is *Thermococcus gammatolerans* RNase H2. As shown by the inventors, an RNase H enzyme is able to enhance signal from a probe. It is believed that the RNase H enzyme cleaves the duplex formed on hybridisation of the oligonucleotide probe to the target nucleic acid sequence, thereby resulting in reduced quenching.

More generally, the sample may be contacted with any nuclease able to specifically degrade the oligonucleotide probe/target nucleic acid sequence duplex.

Amplification of a Target Nucleic Acid Sequence

Where the method of the invention comprises amplification of the target nucleic acid sequence, any suitable method of DNA amplification may be used. Typically, the DNA amplification is carried out under isothermal conditions. The DNA amplification method may comprise strand invasion based amplification, rolling-circle amplification (RCA), strand displacement amplification (SDA), recombinase polymerase amplification (RPA). Strand invasion based amplification (SIBA) is preferred. The above amplification methods typically require the presence of a protein capable of binding single-stranded DNA, and thus the oligonucleotide probe of the invention conveniently allows for detection of amplification in such methods.

The invention thus provides a method for detection of amplification of a target nucleic acid sequence in a sample in the presence of at least one protein capable of binding to single-stranded DNA comprising contacting said sample with an oligonucleotide probe of the invention under conditions promoting amplification of said target nucleic acid sequence.

Such conditions typically comprise the presence of one or more primers and a DNA polymerase enzyme. The skilled person will be able to select suitable primers for a particular target sequence depending on the type of DNA polymerase to be used. Where the DNA polymerase enzyme is an RCA enzyme (such as phi29), random primers or a single species of primer amplifying the target nucleic acid sequence may be used. More typically, the amplification conditions will comprise presence of an upstream primer and a downstream primer for the target nucleic acid sequence.

As discussed above, the oligonucleotide probe may provide a primer function and thus the amplification conditions may comprise the presence of an oligonucleotide probe which acts as a downstream primer and a separate upstream primer (and optionally no other downstream primer(s)) or the presence of an oligonucleotide probe which acts as an upstream primer and a separate downstream primer (and optionally no other upstream primer(s)).

Where SIBA is used, the conditions typically further comprise the presence of a strand invasion oligonucleotide. The features of preferred primers and strand invasion oligonucleotides for SIBA amplification are described in more detail below.

Suitable conditions for amplification of the target nucleic acid sequence further comprise any conditions used to provide for activity of polymerase enzymes known in the art. The conditions typically include the presence of all four dNTPs, dATP, dTTP, dCTP and dGTP or analogues thereof, suitable buffering agents/pH and other factors which are required for enzyme performance or stability. The conditions may include the presence of detergents and stabilising agents. The temperature used is typically isothermal, i.e. constant throughout the amplification process. The temperature used typically depends on the nature of the polymerase enzyme and other enzyme components, and also reflects the hybridisation temperature required for the primers and strand invasion oligonucleotides.

The polymerase used typically has strand-displacement activity. The term "strand displacement" is used herein to describe the ability of a DNA polymerase, optionally in conjunction with accessory proteins, to displace complementary strands on encountering a region of double stranded DNA during DNA synthesis. Suitable DNA polymerases include polI from *E. coli, B. subtilis,* or *B. stearothermophilus,* and functional fragments or variants thereof, and T4 and T7 DNA polymerases and functional fragments or variants thereof. A preferred polymerase is Bsu DNA polymerase or a functional fragment or variant thereof.

The amplification conditions comprise the presence of a protein capable of binding single-stranded DNA. The protein capable of binding single-stranded DNA may be any protein which causes a change in fluorescent signal from an oligonucleotide probe labeled with a fluorophore and quencher in the absence of a complementary template, and which can bind to single-stranded DNA. The protein may be any single-stranded binding protein (SSB) or any protein which is capable of binding single-stranded DNA and also has another functional activity. The protein capable of binding single-stranded DNA may be a recombinase or a recombinase accessory protein or cofactor. The protein capable of binding single-stranded protein may be mesophilic or thermophilic.

The amplification conditions preferably comprise the presence of a recombinase. Any recombinase system may be used in the method of the invention. The recombinase system may be of prokaryotic or eukaryotic origin, and may be bacterial, yeast, phage, or mammalian. The recombinase may polymerise onto a single-stranded oligonucleotide in the 5'-3' or 3'-5; direction. The recombinase may be derived from a myoviridae phage, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, or phage LZ2. In a preferred embodiment, the T4 recombinase UvsX (Accession number: P04529) or a functional variant or fragment thereof is used. The Rad systems of eukaryotes or the recA-Reco system of *E. coli* or other prokaryotic systems may also be used. The recombinase may be *E. coli* RecA.

The conditions may further comprise the presence of recombinase accessory proteins, such as single-stranded binding protein (e.g. T4 gp32, accession number P03695) and recombinase loading agent (e.g. UvsY, accession number NP_049799.2). In a preferred embodiment, the conditions comprise the presence of the T4 gp32, UvsX and UvsY proteins. The recombinase (such as UvsX), and where used the recombinase loading agent (such as UvsY) and single stranded DNA binding protein (such as gp32), can each be native, hybrid or mutant proteins from the same or different myoviridae phage sources. A native protein may be a wild type or natural variant of a protein.

The protein capable of binding single-stranded DNA may alternatively be any protein used to provide single-strand binding activity in a DNA amplification method. The amplification method may be PCR. The protein capable of binding single-stranded DNA may be Extreme Thermostable Single-Stranded DNA Binding Protein (ET-SSB), which may be obtained from New England Biolabs.

The conditions may further comprise other factors used to enhance the efficiency of the recombinase such as compounds used to control DNA interactions, for example proline, DMSO or crowding agents which are known to enhance loading of recombinases onto DNA (Lavery P. et al. J. Biol. Chem. 1992, 267, (13), 9307-9314).

The conditions may also comprise the presence of an ATP regeneration system. Various ATP regeneration systems are known to the person skilled in the art, and include glycolytic enzymes. Suitable components of an ATP regeneration system may include one or more of phosphocreatine, creatine kinase, myokinase, pyrophosphatase, sucrose and sucrose phosphorylase. The conditions may further comprise the presence of ATP.

Additional components such as magnesium ions, DTT or other reducing agents, salts, BSA/PEG or other crowding agents may also be included.

The various components described above may be provided in varying concentrations to provide for DNA amplification. The skilled person can select suitable working concentrations of the various components in practice. Where the oligonucleotide probe overlaps with the sequence of the upstream or downstream primer, any competition observed between binding of the primer and the probe may be minimized by either using a lower concentration of probe or a probe with a reduced region of overlap, such as a probe whose length is shorter than the reverse primer from the 3'-end.

Strand Invasion Based Amplification (SIBA)

The features of the preferred method for amplification of the target nucleic acid sequence, SIBA, are discussed below. The invention provides a method for detection of amplification of a target nucleic acid sequence in a sample in the presence of at least one protein capable of binding to single-stranded DNA comprising contacting said sample with at least one oligonucleotide probe of the invention, at least one upstream primer, at least one downstream primer, and at least one strand invasion oligonucleotide under conditions promoting amplification of said target nucleic acid sequence. As discussed above, the oligonucleotide probe may itself act as the upstream primer or downstream primer, or alternatively separate upstream and downstream primers are provided in combination with the oligonucleotide probe. Each said primer, said probe and said strand invasion oligonucleotide comprise a region complementary to said target nucleic acid sequence. The strand invasion oligonucleotide renders at least a portion of the target nucleic acid sequence single-stranded to allow the binding of each said primer and said probe.

Primers for SIBA

Suitable upstream and downstream primers are selected based on the target nucleic acid sequence of interest, and having regard to the site of binding of the strand invasion oligonucleotide that renders at least a portion of the target nucleic acid sequence single-stranded to allow the binding of the upstream primer and downstream primer. The upstream and downstream primers comprise a sequence that is partly or fully complementary to the target and optionally a 5' and/or 3' flanking non-complementary sequence. Alternatively, the upstream and downstream primers may consist entirely of partly or fully complementary sequence to the target. The length of the primer sequence that is complementary to the target is sufficient to provide specific hybridisation to the target nucleic acid sequence. The length of complementary sequence is typically at least 10 nucleotides, more preferably at least 15, at least 16, or at least 17 nucleotides. The length of complementary sequence may be 10-25, 15-25, 10-30 or 15-30 nucleotides.

It should be understood that the above sequence lengths refer to portions of the primers which may be partly or fully complementary to the target nucleic acid sequence. Mismatches may be present between the primers and the target sequence at particular positions while still allowing for specific amplification and detection of the target sequence, in particular having regard to the combined use of upstream and downstream primers and a strand invasion oligonucleotide to achieve amplification. There may be 1, 2, 3, 4 or 5 mismatches between the complementary region of the primer and the corresponding region of the target sequence.

Typically the upstream and downstream primer will be less than 30 nucleotides in total in length, more preferably less than 25 nucleotides in length, such as 15 to 25, or 15 to 23 nucleotides in length. It is particularly preferred that primers of less than 30 nucleotides in length are used where a recombinase is used for strand invasion. Such primers are not capable of acting as substrates for recombinases.

The upstream (or forward) primer binds to the 5' region of one strand of the duplex target nucleic acid sequence, at a position proximal or overlapping with the 5' binding site of the strand invasion oligonucleotide. The downstream (or reverse) primer binds to the 5' region of the opposing strand of the duplex target nucleic acid sequence to the upstream primer, at a position proximal or overlapping with the 3' binding site of the strand invasion oligonucleotide. The 5' binding sites of the upstream and downstream primers are typically at least 45 nucleotides, more preferably at least 50, at least 55 or at least 60 nucleotides apart on the duplex target sequence.

The upstream and/or downstream primer may have a region of sequence overlap with the sequence of the strand invasion oligonucleotide. The region of sequence overlap is typically 1-8 nucleotides in length, and may be at least 5 or at least 6 nucleotides in length. The downstream primer may also have a region of sequence overlap of 1-8 nucleotides in length with the sequence of the strand invasion oligonucleotide. Alternatively, there may be no sequence overlap between the upstream and/or downstream primer and the strand invasion oligonucleotide, with the primer binding instead at a position that is proximal in the target sequence to the binding site of the strand invasion oligonucleotide.

Where a primer binds proximal to the strand invasion oligonucleotide, typically there is 25 nucleotides or less, more preferably 20 nucleotides or less, 15 nucleotides or less, or 10 nucleotides or less between the relevant binding site of the strand invasion oligonucleotide and the 5' end of the primer. This ensures that the primer is able to hybridise to the single-stranded region created by binding of the strand invasion oligonucleotide.

Preferably, each primer is designed to allow for specific detection of a particular target nucleic acid sequence, such as a particular genotype, or a nucleic acid sequence present in a particular target, such as a particular organism or a particular pathogen. Thus, each primer typically specifically or selectively hybridises to a complementary sequence found only in the target. However, each primer may also hybridise to other sequences, such as sequences found in other species, provided that when used in combination with the second primer, strand invasion oligonucleotide and oligonucleotide probe, specific detection of the target nucleic acid sequence is obtained.

Specific examples of suitable upstream and downstream primers for amplification of target nucleotide sequences in toxigenic *C. difficile* and *S. typhimurium* are provided herein. The invention provides the primers of SEQ ID NOs 21 and 22 or variants thereof for amplification of a target nucleic acid sequence of toxigenic *C. difficile* (such as SEQ ID NO: 26) and the primers of SEQ ID NOs 27 and 28 or variants thereof for amplification of a target nucleic acid sequence of *S. typhimurium* (such as SEQ ID NO: 31).

Variants of SEQ ID NOs 21, 22, 27 and 28 may be oligonucleotides of up to 30 nucleotides in length comprising a region which is partly or fully complementary to at least 10 contiguous nucleotides of the corresponding original primer sequence of SEQ ID NO: 21, 22, 27 and 28. Preferably, said variants will comprise a region which is partly or fully complementary to at least 11, 12, 13, 14 or 15 contiguous nucleotides of the corresponding original primer sequence of SEQ ID NO: 21, 22, 27 and 28. Where the original primer sequence is longer than 16 nucleotides in length, such as up to 21 nucleotides in length (for example SEQ ID NO: 21) the variants may correspondingly comprise a region which is partly or fully complementary to 16, 17, 18, 19 or 20 contiguous nucleotides thereof.

The above variants may comprise a region which has 1, 2, 3, 4, or 5 mismatches (substitutions) with respect to the corresponding region of the original primer sequence (and thus the target sequence) and thus is partly complementary thereto. Thus, for instance, the variants may comprise a region of at least 10 nucleotides in length which has 1, 2, or 3 mismatches, such as 1 or 2 mismatches to a corresponding region of at least ten contiguous nucleotides of the corresponding original primer sequence. The variants may comprise a region of at least 13, 14 or 15 nucleotides in length which has 1, 2, 3, 4 or 5 mismatches, such as 1-3 mismatches to a corresponding region of an equivalent length in the corresponding original primer sequence. Any mismatches in the variant primer sequence may be at least 2, at least 4, at least 5, or at least 10 nucleotides apart.

Alternatively, the variants may comprise a region of at least 10, 11, 12, 13, 14 or 15 nucleotides in length which is in full complementarity with the original primer sequence.

Variants of SEQ ID NOs 21, 22, 27 and 28 may also be oligonucleotides of up to 30 nucleotides in length which have at least 70% sequence identity to the sequence of the corresponding original primer sequence, preferably at least 75%, at least 80%, more preferably at least 85%, at least 90%, at least 95% sequence identity.

Additionally, the variant primers may comprise 5' and/or 3' flanking nucleotide sequence(s) to the region which is partly or fully complementary to the original primer sequence. The 5' and/or 3' flanking sequence(s) may be non-complementary to the target nucleic acid sequence, or may be complementary in sequence to the regions that flank the binding region of the original primer in the target nucleic acid sequence, such as the 5-10 nucleotides 5' and/or 3' to the binding region of the original primer in the target nucleic acid sequence.

Strand Invasion Oligonucleotide for SIBA

A suitable strand invasion oligonucleotide is selected based on the target nucleic acid sequence of interest, and having regard to the site of binding of the upstream and downstream primers and the requirement for the strand invasion oligonucleotide to render the target nucleic acid sequence single-stranded in the relevant regions to allow for the binding of the upstream primer and downstream primer.

The strand invasion oligonucleotide comprises a sequence that is complementary to the target and optionally additional flanking non-complementary sequence(s). The length of the sequence that is complementary to the target may be determined by the skilled person empirically and is sufficient to provide for efficient strand invasion of the target nucleic acid sequence, optionally under isothermal conditions. The complementary sequence may comprise RNA-DNA complementary base pairing and modified nucleotides. Typically, the length of complementary sequence is at least 25 or at least 27 nucleotides, typically at least 30 nucleotides, such as least 32, at least 33 or at least 35 nucleotides, more preferably at least 36, 37, 38, 39 or 40 nucleotides in length or greater. The length of complementary sequence may be 30-50, 32-50, 35-50, 40-50, 35 to 48, 35 to 46, 38 to 45 or 40 to 45 nucleotides in length.

It should be understood that the above sequence lengths refer to a portion of the strand invasion oligonucleotide which may be partly or fully complementary to the target nucleic acid sequence. Mismatches may be present between the strand invasion oligonucleotide and the target sequence at particular positions while still allowing for specific amplification and detection of the target sequence, in particular having regard to the combined use of upstream and downstream primers and a strand invasion oligonucleotide to achieve amplification. There may be 1, 2, 3, 4, 5, 6, 7, or 8 mismatches between the complementary region of the strand invasion oligonucleotide and the corresponding region of the target sequence, depending on the total length of complementary sequence.

The complementary sequence of the strand invasion oligonucleotide hybridises to a portion of the target sequence intervening the binding regions for the upstream and downstream primers (and typically overlapping with one or more thereof). The strand invasion oligonucleotide may have a region of overlap of 1-8 nucleotides, such as a region of at least 5 or at least 6 nucleotides in length, with the upstream and/or downstream primers. The 5' portion of the complementary sequence of the strand invasion oligonucleotide typically binds within 25 nucleotides or less, more preferably 20 nucleotides or less from the 5' boundary of the duplex target nucleotide sequence to be melted (the amplicon).

The strand invasion oligonucleotide optionally further comprises non-complementary sequence region(s) to the target that flank the complementary sequence region. The strand invasion oligonucleotide may comprise a non-complementary 5' region which may be of any nucleotide sequence. The 5' non-complementary region is typically at least 3 nucleotides in length, more typically at least 6, at least 8, preferably at least 10, at least 12 or at least 14 nucleotides in length. The 5' non-complementary region may assist binding of recombinase. The strand invasion oligonucleotide may comprise a 3' non-complementary region typically of 1-3 nucleotides in length which comprises nucleotides which block polymerase extension such as invdT.

The strand invasion oligonucleotide is typically at least 30 nucleotides in length where a recombinase is used in conjunction with the oligonucleotide. The strand invasion oligonucleotide is preferably at least 35, at least 40 or at least 45 nucleotides in length, more preferably at least 50, and may be at least 55 nucleotides in length or greater. The strand invasion oligonucleotide may be 40-70, 45-70, 45-70, 50-70, 55-70, 45-65, 50-65, 50-60 or 55-65 nucleotides in length.

Typically the strand invasion oligonucleotide has a non-extendible 3'terminus, such that it cannot serve as a substrate for DNA amplification, and the target sequence is then only amplified on the further binding of the specific upstream and downstream primers. This avoids formation of non-specific amplification products. The strand invasion oligonucleotide may comprise one, two, three, four, five, six, seven, eight or more modified nucleotides in its 3' region, such as in the 10-15 or 10-20 nucleotides from the 3' terminus. The strand-invasion oligonucleotide may comprise a 3' modification of the 3' terminal nucleotide, and may be a dideoxynucleotide, or comprise a 3' amino-allyl group, a 3'carbon spacer, 3'phosphate, 3'biotin, 3'sialyl, or 3'thiol. The 3' nucleotide may be a nucleotide incorporated in a reversed orientation by a 3'-3' linkage. Alternatively or additionally, the 3' region of the strand-invasion oligonucleotide may comprise nucleotides with poor substrate capability for DNA polymerases, such as PNA (peptide nucleic acid) nucleotides, LNA (locked nucleic acid), 2'-5' linked DNA or 2'-O-methyl RNA, or combinations thereof.

Where the strand-invasion oligonucleotide is a PNA oligomer comprised wholly of PNA, such an oligonucleotide can destabilise and invade duplex DNA in the absence of a recombinase enzyme. Thus, where a PNA oligonucleotide is used, the methods of the invention may be performed without presence of a recombinase enzyme.

Specific examples of suitable strand invasion oligonucleotides for target nucleotide sequences in toxigenic *C. difficile* and *S. typhimurium* are provided herein. The invention provides the strand invasion oligonucleotide of SEQ ID NO: 23 or a modified derivative or variant thereof for amplification of a target nucleic acid sequence of toxigenic *C. difficile* (such as SEQ ID NO: 26) and the strand invasion oligonucleotide of SEQ ID NO 29 or a modified derivative or variant thereof for amplification of a target nucleic acid sequence of *S. typhimurium* (such as SEQ ID NO: 31).

As discussed above, it is preferred that a strand invasion oligonucleotide used in the invention comprises one or more modified oligonucleotides in its 3' region to block its use as a polymerase substrate. Thus, a modified derivative of SEQ ID NO: 23 or 29 may comprise one, two, three, four, five, six, seven, eight or more modified nucleotides in its 3' region, typically in the 10-15 or 10-20 nucleotides from the 3' terminus. The modifications may be selected from any of those discussed above. The modified derivative may be a PNA oligomer of corresponding sequence to SEQ ID NO: 23 or 29.

Variants of SEQ ID NOs 23 and 29 are typically oligonucleotides of greater than 30 nucleotides, more preferably at least 35, at least 40, or at least 45 nucleotides in length, comprising a region which is partly or fully complementary to at least 30 contiguous nucleotides of the corresponding original target-complementary sequence present in SEQ ID NO: 23 or 29. Preferably, said variants will comprise a region which is partly or fully complementary to at least 32, 35, 37, 40, 42 or 45 contiguous nucleotides of the target-complementary sequence present in SEQ ID NO: 23 or 29.

The above variants may comprise a region which has 1, 2, 3, 4, 5, 6, 7 or 8 mismatches (substitutions) with respect to the corresponding target-complementary region of the original strand invasion oligonucleotide of SEQ ID NO: 23 or 29 (and thus the target sequence) and thus is partly complementary thereto. Thus, for instance, the variants may comprise a region of at least 30 nucleotides in length which has 1, 2, 3, or 4, such as 1-4 or 1-3 mismatches to a corresponding region of at least 40 contiguous nucleotides of the corresponding original strand invasion oligonucleotide. The variants may comprise a region of at least 35, 40, 42, or 45 nucleotides in length which has 1, 2, 3, 4, 5 or 6, such as 1-5, or 1-3 mismatches to a corresponding region of an equivalent length in the corresponding original strand invasion oligonucleotide. Any mismatches in the variant strand invasion oligonucleotide sequence may be at least 2, at least 4, at least 5, or at least 10 nucleotides apart.

Alternatively, the variants may comprise a region of at least 32, 35, 37, 40, 42 or 45 nucleotides in length which is in full complementarity with the target-complementary region of the original strand invasion oligonucleotide.

Variants of SEQ ID NOs 23 and 29 may also be oligonucleotides of greater than 30 nucleotides in length comprising a target-complementary region which has at least 70% sequence identity to the target-complementary sequence of the corresponding original strand invasion oligonucleotide, preferably at least 75%, at least 80%, more preferably at least 85%, at least 90%, at least 95% sequence identity.

The variant strand invasion oligonucleotides may comprise 5' and/or 3' flanking nucleotide sequence(s) to the region which is partly or fully complementary to the original strand invasion oligonucleotide sequence. The 5' and/or 3' flanking sequence(s) may be non-complementary to the target nucleic acid sequence, or may be complementary in sequence to the regions that flank the binding region of the original strand invasion oligonucleotide in the target nucleic acid sequence, such as the 5-10 or 5-15 nucleotides 5' and/or 3' to the binding region of the original strand invasion oligonucleotide in the target nucleic acid sequence.

The remaining sequence of the variant strand invasion oligonucleotides is typically unrelated to the target sequence, and also typically unrelated to the original strand invasion oligonucleotide.

The variant strand invasion oligonucleotides further comprise one or more modified oligonucleotides in their 3' region such as, two, three, four, five, six, seven, eight or more modified nucleotides, which may be in the 10-15 or 10-20 nucleotides from the 3'terminus The modifications may be selected from any of those discussed above.

Detection of Target Nucleotide Sequences

The invention provides particular combinations of upstream and downstream primers, oligonucleotide probes and strand invasion oligonucleotides for detection of target nucleotide sequences. Thus, the invention provides a method for detection of a target nucleic acid sequence of toxigenic *C. difficile* in a sample in the presence of at least one single-stranded DNA binding protein comprising contacting said sample with an oligonucleotide probe of SEQ ID NO: 24 or 25 or a variant of either thereof as described above, an upstream primer of SEQ ID NO: 21 or a variant thereof as described above, a downstream primer of SEQ ID NO: 22 or a variant thereof as described above, and a strand invasion oligonucleotide of SEQ ID NO: 23 or a modified derivative or variant thereof as described above, under conditions promoting amplification of said target nucleic acid sequence. Such a method may comprise detection of the target nucleic acid sequence of SEQ ID NO: 26.

The invention further provides a method for detection of a target nucleic acid sequence of *S. typhimurium* in a sample in the presence of at least one single-stranded DNA binding protein comprising contacting said sample with an oligonucleotide probe of SEQ ID NO: 30 or a variant thereof as described above, an upstream primer of SEQ ID NO: 27 or a variant thereof as described above, a downstream primer of SEQ ID NO: 28 or a variant thereof as described above, and at least one strand invasion oligonucleotide of SEQ ID NO: 29 or a modified derivative or variant thereof as described above, under conditions promoting amplification of said target nucleic acid sequence. Such a method may comprise detection of the target nucleic acid sequence of SEQ ID NO: 31.

The invention further provides a method for detection of the target nucleic acid sequence of SEQ ID NO: 20 in a sample in the presence of at least one single-stranded DNA binding protein comprising contacting said sample with an oligonucleotide probe of SEQ ID NO: 13 or 14 or a variant thereof as described above, an upstream primer of SEQ ID NO: 11 or a variant thereof, a downstream primer of SEQ ID NO: 12 or a variant thereof, and at least one strand invasion oligonucleotide of SEQ ID NO: 15 a modified derivative or variant thereof, under conditions promoting amplification of said target nucleic acid sequence. Variants of SEQ ID NOs 11 and 12 may be selected according to the same criteria described above for variants of SEQ ID NOs 21, 22, 27 and 28. Variants and modified derivatives of SEQ ID NO 15 may be selected according to the same criteria described above for variants of SEQ ID NOs 23 and 29.

The invention also provides a method for detection of the target nucleic acid sequence of SEQ ID No: 34 in a sample in the presence of at least one single-stranded DNA binding protein comprising contacting said sample with an oligonucleotide probe of any one of SEQ ID NOs 3 to 10 or a variant thereof.

Products of the Invention

Nucleic Acids

The invention further provides an oligonucleotide probe comprising a fluorophore, a quencher and a region complementary to a target nucleic acid sequence as a product per se. The sequence of the oligonucleotide probe comprises at least 20% RNA nucleotides, modified RNA nucleotides and/or PNA nucleotides. The oligonucleotide probe product of the invention may be any oligonucleotide probe described above for use in the methods of the invention. The invention also specifically provides an oligonucleotide probe of SEQ ID NOs: 3 to 10, 13, 14, 24, 25 or 30 or a variant of any thereof as described above.

Compositions

The invention also provides a composition and formulation comprising an oligonucleotide probe of the invention. The composition may be for example a solution, lyophilisate, suspension, or an emulsion in an oily or aqueous vehicle. The composition may further comprise one or more oligonucleotide components selected from an upstream primer, a downstream primer and a strand invasion oligonucleotide. The composition may further comprise one or more proteins selected from a DNA polymerase, protein capable of binding to single-stranded DNA, a recombinase and a recombinase accessory protein. The composition preferably comprises the oligonucleotide probe and in addition (i) a strand invasion oligonucleotide comprising a region complementary to the target nucleic acid sequence and/or (ii) at least one protein capable of binding to single-stranded DNA. Probe, primer and strand invasion oligonucleotide components of the composition are each designed for detection of the target nucleic acid sequence.

The composition may comprise an oligonucleotide probe of SEQ ID NO: 24 or 25 or a variant thereof in combination with (i) an upstream primer of SEQ ID NO: 21 or a variant thereof, (ii) a downstream primer of SEQ ID NO: 22 or a variant thereof and/or (iii) a strand invasion oligonucleotide of SEQ ID NO: 23 or variant thereof. Additionally, or alternatively the composition may comprise an oligonucleotide probe of SEQ ID NO: 30 or a variant thereof in combination with (i) an upstream primer of SEQ ID NO: 27 or a variant thereof, (ii) a downstream primer of SEQ ID NO: 28 or a variant thereof and/or (iii) a strand invasion oligonucleotide of SEQ ID NO: 29 or variant thereof. Additionally, or alternatively, the composition may comprise an oligonucleotide probe of any one of SEQ ID NOs 17 to 19 and 32 or a variant thereof in combination with (i) an upstream primer of SEQ ID NO: 11 or a variant thereof, (ii) a downstream primer of SEQ ID NO: 12 or a variant thereof and/or (iii) a strand invasion oligonucleotide of SEQ ID NO: 15 or variant thereof.

Kits

The invention further provides a kit comprising at least one oligonucleotide probe of the invention. The kit optionally further comprises instructions for use in a method of the invention. The kit may comprise a means for detection of amplified DNA. The kit may comprise an upstream primer and/or a downstream primer. The kit may comprise a strand invasion oligonucleotide. Each of the above oligonucleotides may be provided in the kit as a mixture, or in separate containers.

The kit or composition optionally comprises one or more of a DNA polymerase, a recombinase, and recombinase accessory proteins. Preferably, the DNA polymerase is Bsu polymerase. Preferably, the recombinase is bacteriophage T4 UvsX, optionally in combination with the recombinase accessory proteins UvsY and gp32. The kit or composition may further comprise dNTPs, suitable buffers and other factors which are required for DNA amplification in the method of the invention as described above.

The kit may comprise any combination of oligonucleotide probe, upstream primer, downstream primer and/or strand invasion oligonucleotide described above in connection with the methods and compositions of the invention.

Applications for Detection of Target Nucleic Acid Sequences

The methods of the invention may be used in any application where a target nucleic acid sequence is desired to be detected.

Methods for Diagnosis

The present invention is particularly advantageous in the medical setting. The detection methods of the invention provide a highly specific test to allow for determination of whether a clinical sample contains a target nucleic acid sequence. The method may be applied to a range of disease settings. The invention provides a method for diagnosis of a disease in a subject, comprising carrying out a method of detection of a target nucleic acid sequence of the invention in a sample from said subject to detect a target nucleic acid sequence associated with said disease.

Such a method may be for diagnosis of an infection by a pathogen in a subject, comprising detection of a target nucleic acid sequence from said pathogen. The determination of whether or not the pathogen is present may be in the context of any disease or illness present or suspected of being present in a patient. Such diseases may include those caused by, linked to, or exacerbated by the presence of the pathogen. Thus, a patient may display symptoms indicating the presence of the pathogen, and a sample may be obtained from the patient in order to determine the presence of pathogen by the method described above.

Any pathogen may be detected. The pathogen may be a virus or bacterium or parasite. The pathogen may be a pathogen such as, but not limited to, fungi, viruses including Human Papilloma Viruses (HPV), HIV, HSV2/HSV1, Influenza virus (types A, B and C), Polio virus, RSV virus, Rhinoviruses, Rotaviruses, Hepatitis A virus, Norwalk Virus Group, Enteroviruses, Astroviruses, Measles virus, Parainfluenza virus, Mumps virus, Varicella-Zoster virus, Cytomegalovirus, Epstein-Barr virus, Adenoviruses, Rubella virus, Human T-cell Lymphoma type I virus (HTLV-I), Hepatitis B virus (HBV), Hepatitis C virus (HCV), Hepatitis D virus, Pox virus, Marburg and Ebola; bacteria including *Mycobacterium tuberculosis, Chlamydia, Neisseria gonorrhoeae, Shigella, Salmonella, Vibrio cholerae, Treponema pallidum, Pseudomonas, Bordetella pertussis, Brucella, Franciscella tularensis, Helicobacter pylori, Leptospira interrogans, Legionella pneumophila, Yersinia pestis, Streptococcus* (types A and B), Pneumococcus, Meningococcus, *Haemophilus* influenza (type b), *Toxoplasma gondii*, Campylobacteriosis, *Moraxella catarrhalis*, Donovanosis, and Actinomycosis; fungal pathogens including Candidiasis and Aspergillosis; parasitic pathogens including *Taenia*, Flukes, Roundworms, Amoebiasis, Giardiasis, *Cryptosporidium, Schistosoma, Pneumocystis carinii*, Trichomoniasis and Trichinosis.

Particular pathogens of interest include toxigenic *C. difficile* and *S. typhimurium* and methods and combinations of oligonucleotides suitable for diagnosis of infections by these pathogens are described above.

A particularly preferred embodiment of the invention is the identification of toxigenic *C. difficile* present in patients having a gastrointestinal tract infection, in particular having symptoms of diarrhoea.

The invention thus provides a diagnostic method for gastrointestinal illnesses, such as diarrhoea that are caused by toxigenic *C. difficile* and *S. Typhimurium*. The diagnostic method may further comprise detecting antibiotic resistance markers and virulence markers. The method provides for a dramatic improvement in the patient management of gastrointestinal illnesses because it allows for the optimal therapeutic treatment for a given patient. Thereby the test would reduce the length of hospital stays, the frequency of re-admission and reduce costs.

The diagnostic method may conveniently be performed based on nucleic acid derived from a sample of a patient, providing an indication to clinicians whether the gastrointestinal illness is due to an infection by toxigenic *C. difficile* or *S. typhimurium*. The diagnostic method may for instance provide an indication as to the toxinotype and virulence of *C. difficile* and whether the *C. difficile* is resistant to any antibiotics. Depending on the outcome of the test the medical treatment can then be optimised, for example by use of antibiotics.

Detection of *Salmonella typhimurium*

In a broader aspect, the invention provides a method for detecting *S. typhimurium* in a sample, said method comprising contacting said sample with at least one upstream primer, at least one downstream primer and at least one strand invasion oligonucleotide under conditions promoting amplification of a target nucleic acid sequence comprising SEQ ID NO: 31, wherein each said primer and said strand invasion oligonucleotide comprises a region complementary to said target nucleic acid sequence; and wherein said strand invasion oligonucleotide renders at least a portion of the target nucleic acid sequence single-stranded to allow the binding of said upstream primer and a downstream primer.

Preferably, said method further comprises contacting said sample with at least one oligonucleotide probe comprising a fluorophore, a quencher and a region complementary to said target nucleic acid sequence. Typically, said oligonucleotide probe comprises at least 20% RNA nucleotides, modified RNA nucleotides and/or PNA nucleotides and is thus an oligonucleotide probe of the invention as described above. Typically, said method for detecting *Salmonella typhimurium* is carried out in the presence of at least one protein capable of binding to single-stranded DNA. Typically, said protein capable of binding to single-stranded DNA is a recombinase.

Preferably, the upstream primer comprises the sequence of SEQ ID NO: 27 or a variant thereof, the downstream primer comprises the sequence of SEQ ID NO: 28 or a variant thereof, and the strand invasion oligonucleotide comprises the sequence of SEQ ID NO: 29 or a variant thereof.

The following Examples illustrate the invention.

EXAMPLES

Example 1

Affinity of Different Oligonucleotides for Single-Stranded DNA Binding Proteins

The effect of proteins capable of binding to single-stranded DNA on the signal produced by single-stranded oligonucleotide probes containing fluorophore and quencher was investigated. The oligonucleotide probes were composed of natural DNA or RNA, or modified nucleic acids, such as 2'-fluoro RNA, 2'-O-methyl RNA, PNA, or LNA. The lengths of the LNA and PNA probes were 12 and 14 bases respectively compared to the other probes (16-21 bases in length). Shorter LNA and PNA probes were used due to their higher melting temperatures. The concentration of the oligonucleotide probes in the affinity assays was 100 nM, except for PNA which was 800 nM.

The oligonucleotide probes were incubated in the presence or absence of 200 nM complementary template (SEQ ID NO: 34 for probes with SEQ ID NO 1-8, or SEQ ID NO: 44 for probes with SEQ ID NO 9 or 10) and 5 µM UvsX in buffer containing 20 mM Tris-acetate pH 8.0, 10 mM Magnesium acetate, 2 mM ATP, 60 mM Tris-Phosphocreatine and 0.025 U/µl Creatine Kinase. Fluorescence was measured after 20 minutes incubation at 40 degrees centigrade.

Incubation of all oligonucleotide probes with their complementary template led to an increase in fluorescence signal compared with signal produced in the absence of the complementary template (FIG. 1a). The presence of bacteriophage T4 UvsX in the absence of a complementary template however also led to an significant increase in fluorescence signal with natural DNA oligonucleotide probes (SEQ ID NOs: 1 and 2), as shown in FIG. 1a. A possible explanation of this observation was that UvsX destabilizes secondary conformation of a DNA probe resulting to an increased distance between the probe and the quencher and increased probe signal even in the absence of a complementary template. This non-specific activation of the probe would be expected to lead to poor signal to background ratio when monitoring DNA amplification in a reaction containing UvsX.

In contrast, oligonucleotide probes having identical sequence but composed of RNA (SEQ ID NOs: 3 and 4) or modified RNA (SEQ ID NOs: 5, 6, 7, 8) or of LNA (SEQ ID NO: 9) or PNA (SEQ ID NO: 10) remained quenched in the presence of UvsX with significant signal increase only occurring in the presence of a complementary template.

The effect of the single-strand binding protein, bacteriophage T4 gp32 (New England Biolabs), on signal from the same oligonucleotide probes used with UvsX was also elucidated. Similar concentrations of oligonucleotide probes to those used with UvsX were incubated in the presence or absence of 0.25 mg/ml of gp32 and 200 nM complementary template ((SEQ ID NO: 34 for probes with SEQ ID NO 1-8 or SEQ ID NO: 44 for probes with SEQ ID NO: 9 or 10) in a buffer containing 20 mM Tris-acetate pH 7.9, 50 mM potassium acetate, 10 mM Magnesium Acetate and 1 mM DTT.

Figure 1B:
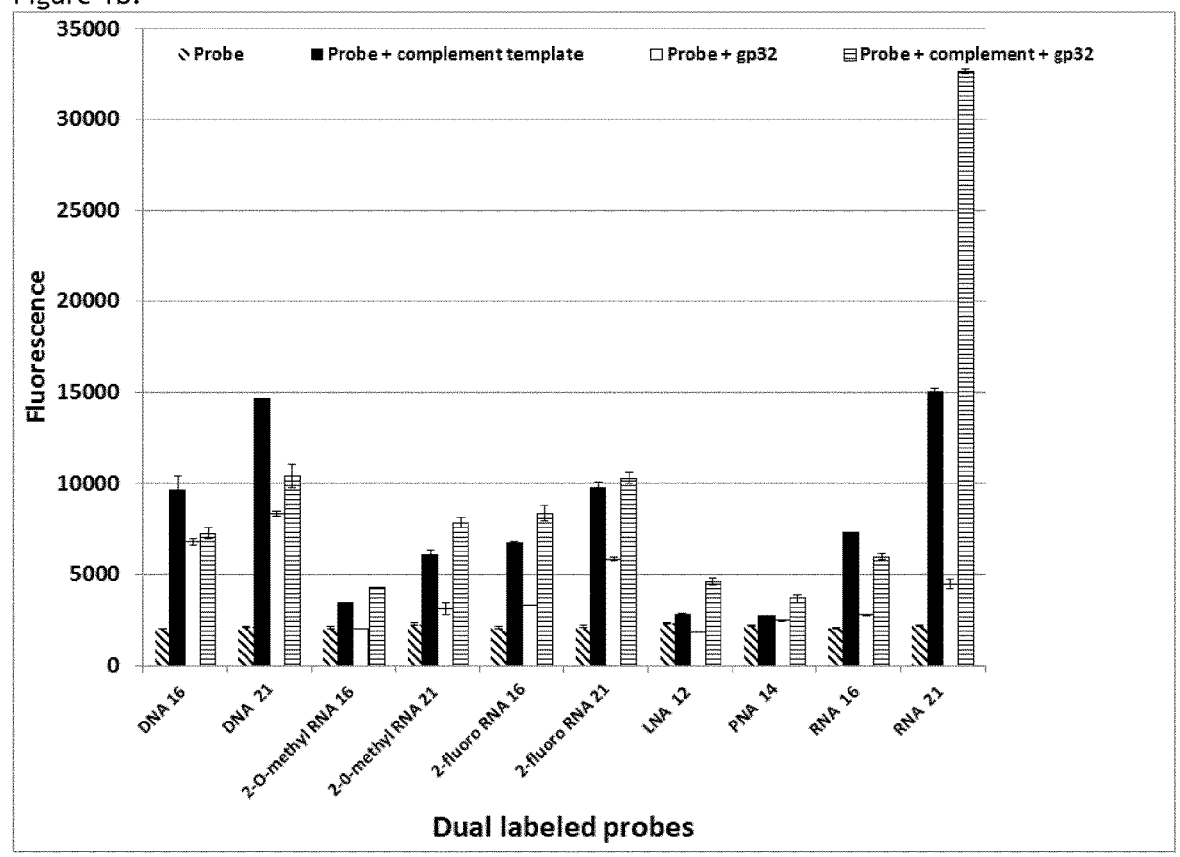

The presence of gp32 again resulted in a significant increase in signal of DNA probes (SEQ ID NOs: 1 and 2) in the absence of complement template as shown in FIG. 1b. There was also no significant difference between signal produced from the DNA probes in presence or absence of complementary template when gp32 was present. Accordingly, dual labeled natural DNA probes are unsuitable for target detection in reactions containing T4 gp32.

In contrast, RNA (SEQ ID NO: 3 and 4) or modified RNA (SEQ ID NOs: 5, 6, 7, 8), LNA (SEQ ID NO: 9) and PNA (SEQ ID NO: 10) probes displayed little or no significant increase in fluorescence in the presence of T4 gp32.

The oligonucleotide probes were also tested with reagent conditions used in an isothermal strand invasion based amplification method utilising both a single-strand binding protein and a recombinase for amplification. The reagent components in the reaction were 10 mM Tris-acetate pH 8.0, 10 mM Magnesium acetate, 5% DMSO, 5% PEG 1000, 4 mM DTT, 0.5 mM EDTA, 0.1 mg/ml BSA, 150 mM Sucrose, 2 mM ATP, 200 µM DNTP's, 1:100,000 SYBR Green I, 60 mM Tris-Phosphocreatine. The proteins in the reaction were 250 ng/µl of gp32, 5 µM UvsX, 0.0625 U/µl BSU, 0.0125 U/µl sucrose phosphorylase and 0.025 U/µl creatine Kinase (Sigma-Aldrich St. Louis, Mo., U.S.A). The concentrations of primers and strand invasion oligonucleotides were 200 nM. The concentration of probe used was 200 nM except where otherwise stated.

All reactions were prepared without the target DNA or Magnesium acetate. The reactions were then either started by adding an appropriate amount of target DNA prepared in magnesium acetate or with magnesium acetate alone. Real-time detection of fluorescent signal generated in reactions was performed in 96-well plates at 40° C.

Figure 1C:
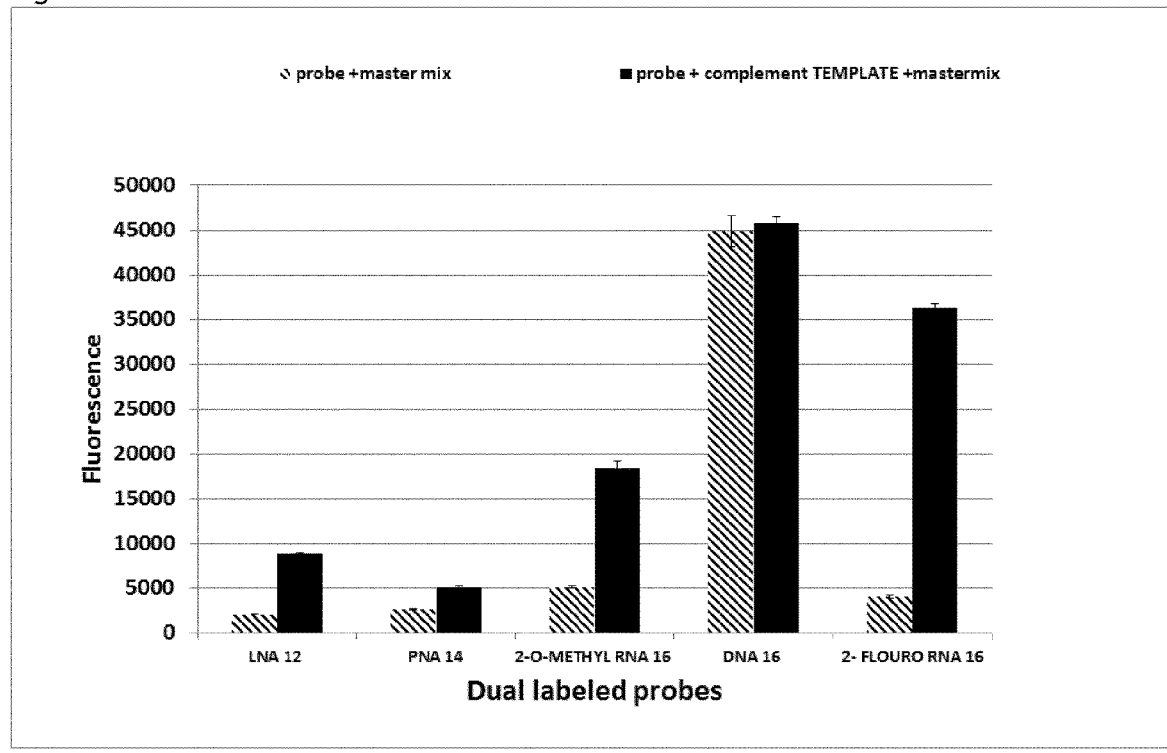

On incubation of the above reagent composition (devoid of primers and strand invasion oligonucleotides) with DNA probes (SEQ ID NOs 1 and 2), there was no difference in the signal produced in the presence or absence of a complementary template (FIG. 1c). Thus, natural DNA containing probes are undesirable for use in DNA amplification reactions where a single-strand binding protein and/or a recombinase are employed. In contrast, RNA (SEQ ID NO: 3 and 4) or modified RNA (SEQ ID NOs: 5, 6, 7, 8), LNA (SEQ ID NO: 9) and PNA (SEQ ID NO: 10) probes were shown to generate an increase in signal only when a complementary template was present. Thus, RNA, modified RNA, LNA and PNA probes are suitable for DNA amplification reactions where a single-strand binding protein and/or a recombinase are employed.

Figure 1D:
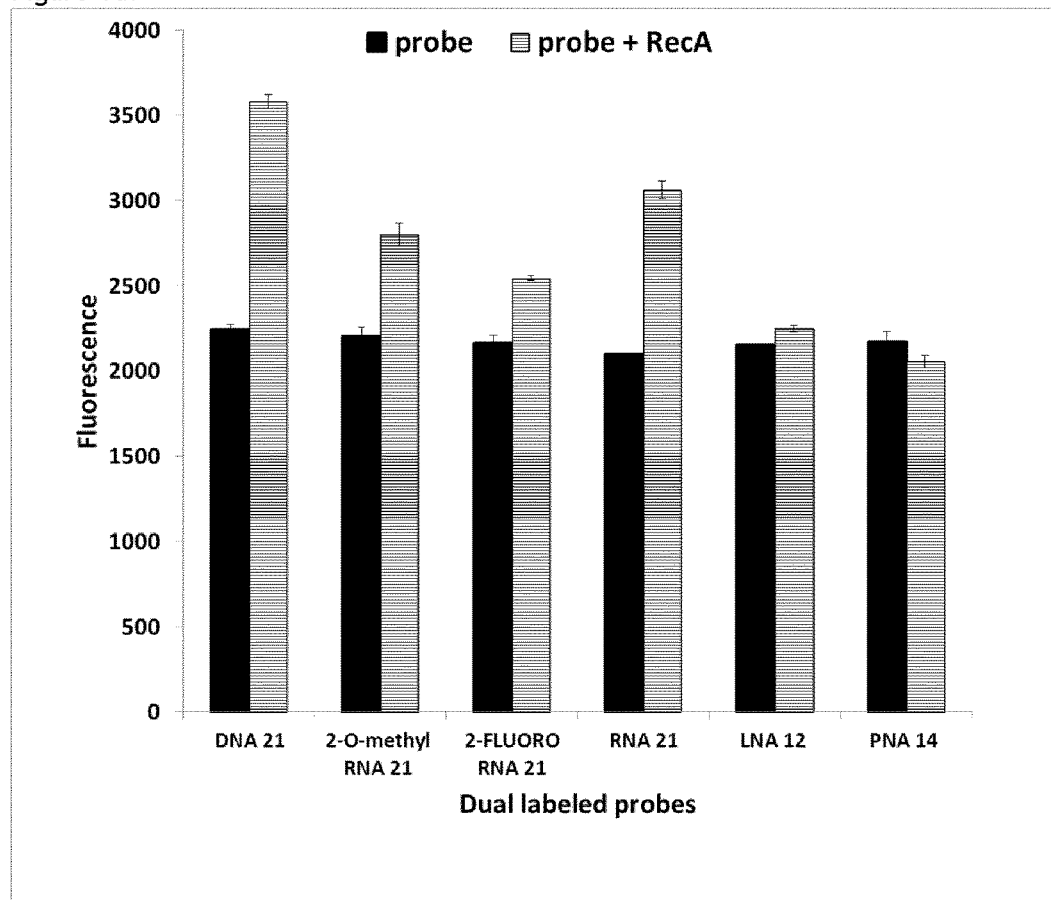

The effect of *Escherichia coli* recombinase, RecA (New England Biolabs) on signal from oligonucleotide probes was also elucidated (FIG. 1d). Similar concentrations of oligonucleotide probes to those used in FIGS. 1a and 1b were incubated in the presence or absence of 100 µg/ml of RecA in a buffer containing 70 mM Tris-HCl pH 7.6.10 mM MgCl$_2$, 5 mM DTT and 10 mM ATP. The presence of RecA also resulted in an increased signal of natural DNA containing probes (FIG. 1d, DNA21 [SEQ ID NO:2]). However, the increase was not as high as that seen with T4 UvsX. Nonetheless, as seen with T4 UvsX, incubation of RecA with probes containing RNA (RNA21 SEQ ID NO: 4), 2'-fluoro RNA (2-FLUORO RNA21, SEQ ID NO: 8), 2'-O-methyl RNA (2-O-METHYL RNA21, SEQ ID NO: 6), LNA (SEQ ID NO: 9) or PNA (SEQ ID NO: 10) did not result in any significant increase in signal.

Figure 1E:
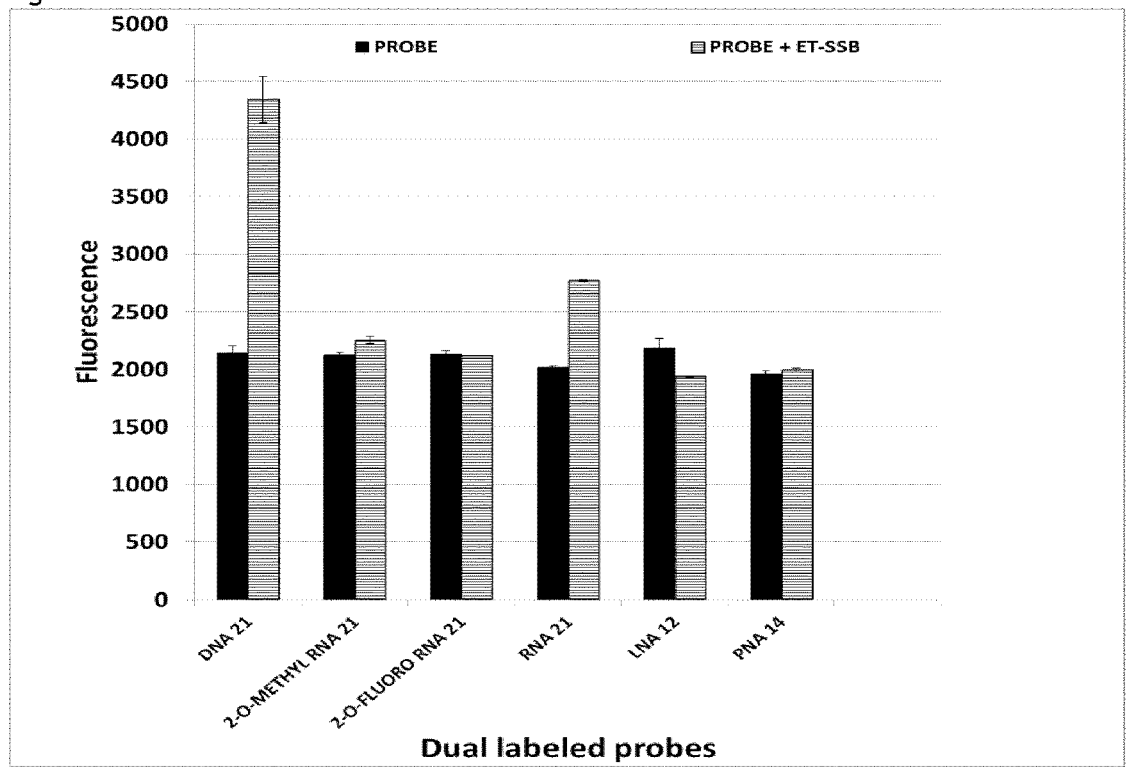

The effect of Extreme Thermostable Single-Stranded DNA Binding Protein, ET-SSB (New England Biolabs) on these oligonucleotide probes was additionally elucidated (FIG. 1e). Unlike T4-gp32 whose activity is lost if used at temperature above 50° C., ET-SSB still retains its activity at 95° C. ET-SSB is therefore a suitable choice, if single strand binding proteins are required in reaction performed at high temperature such as polymerase chain reaction (PCR) or DNA sequencing. Similar concentrations of oligonucleotide probes to those used in FIGS. 1a and 1b were incubated in the presence or absence of 50 µg/ml of ET-SSB in a buffer containing 20 mM Tris-acetate pH 7.9, 50 mM potassium acetate, 10 mM Magnesium Acetate and 1 mM DTT. The presence of ET-SSB also resulted in a significant increase in signal of natural DNA containing probes (FIG. 1e, DNA21 SEQ ID NO2). Dual labeled probes containing natural DNA alone are thus unsuitable in reactions containing ET-SSB. In contrast probes containing RNA (RNA21, SEQ ID NO: 4), 2'-fluoro RNA (2-FLUORO RNA21, SEQ ID NO: 8), 2'-O-methyl RNA (2-O-METHYL RNA21, SEQ ID NO: 6), LNA (SEQ ID NO: 9) or PNA (SEQ ID NO: 10) were more resistant to ET-SSB. These modified probes are therefore more suitable for reactions performed in the presence of single strand binding proteins like ET-SSB.

Example 2

Figure 2A:
FIG. 2 shows amplification of a target DNA by strand invasion based amplification. A) Configuration of the primers, probe, strand invasion/intermediate oligonucleotide (IO) and target DNA. B) Real-time monitoring of amplification detected by using SYBR Green. C) Real-time monitoring of amplification detected using 2'-fluoro RNA probe SB-2FLUORO (SEQ ID NO: 17). D) Real-time monitoring of amplification detected using LNA probe (SB-LNA SEQ ID NO: 18). E) Real-time monitoring of amplification detected using natural DNA probe (SB-DNA SEQ ID NO: 16). In B) to E) NTC=no template control, dilutions of template shown. Reactions were performed in duplicate. X-axis: Time (minutes). Y-axis for each chart: fluorescence (arbitrary units).

Detection of Strand-Invasion Based Amplification (SIBA™) Using Different Oligonucleotide Probes Three probes composed of natural DNA (SEQ ID NO: 16), 2'-fluoro RNA (SEQ ID NO: 17) and LNA (SEQ ID NO: 18) labelled with a fluorophore and a quencher were tested. The configuration of the forward primer (SEQ ID NO: 11), reverse primer (SEQ ID NO: 12), probe, strand invasion oligonucleotide (SEQ ID NO: 15), and target nucleic acid sequence (SEQ ID NO: 20) is summarized in FIG. 2a. The probes are designed to overlap partly a downstream region of the reverse primer (SEQ ID NO: 12), and therefore bind the same region on the target template as the reverse primer.

Figure 2B:
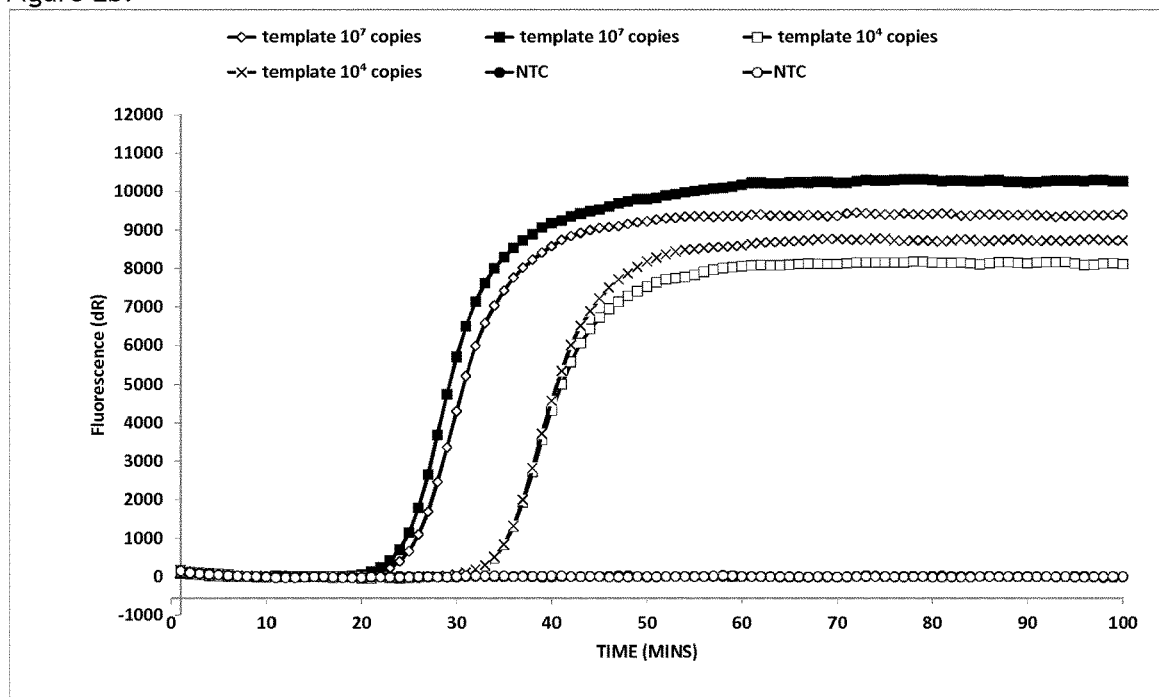
Figure 2C:
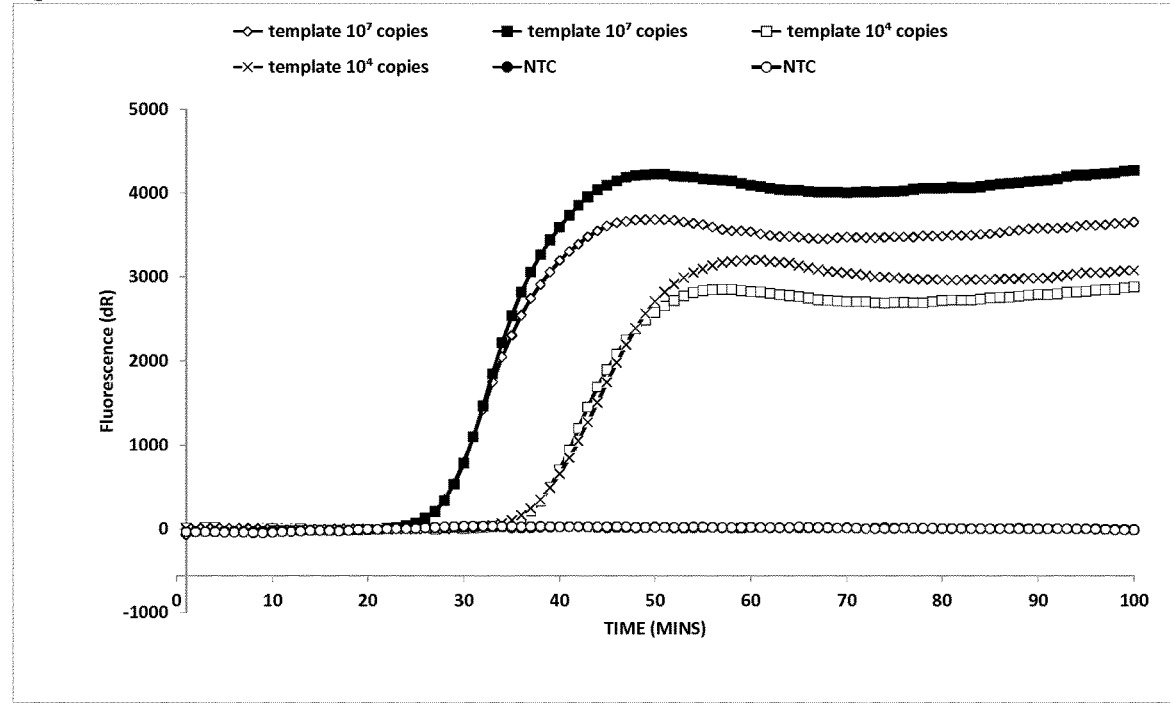
Figure 2D:
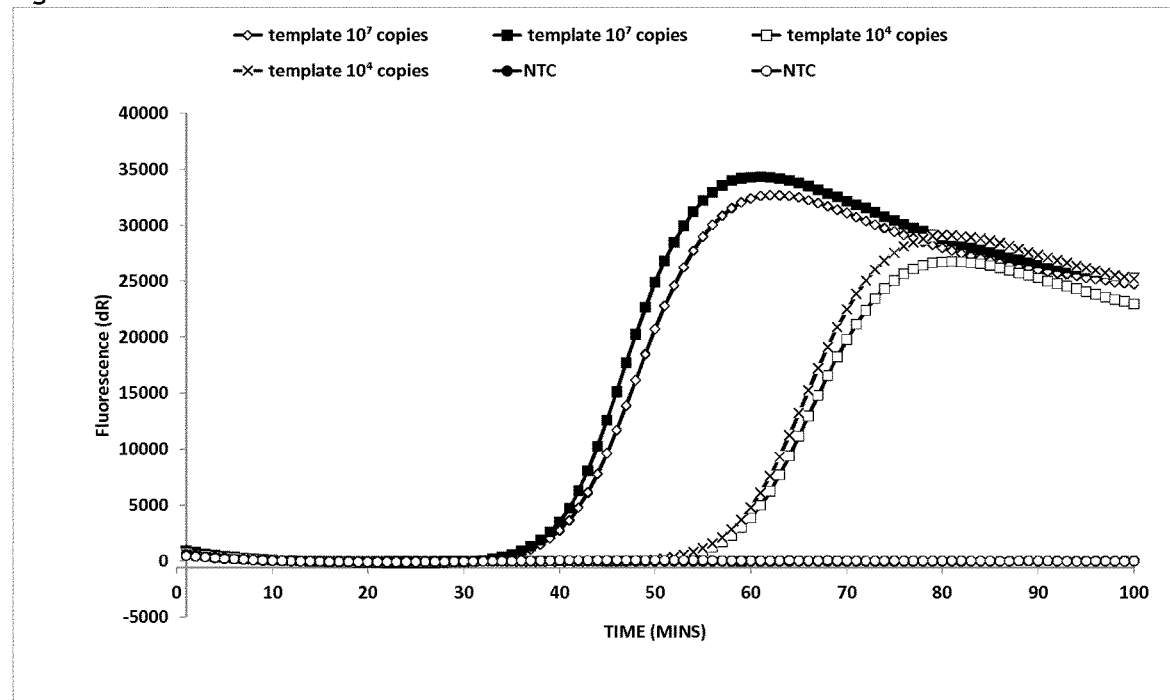

An artificial target DNA (SEQ ID NO: 20) was real-time amplified and detected using the probe, primers and strand invasion oligonucleotide in a strand-invasion based amplification reaction as described in Example 1. Amplification of target DNA was only obtained in reactions that contained the target DNA, while no template control (NTC) did not produce amplification, as shown in reactions detected using SYBR Green I dye (FIG. 2b). Specific detection of template-dependent amplification was also observed where 2'-fluoro RNA or LNA probes of SEQ ID NOs 17 and 18, respectively, were used (FIGS. 2c and 2d). A slight delay in the onset of amplification was observed in samples detected with 2'-fluoro RNA or LNA containing probes, as a result of competition between the reverse primer and the probe. This competition can be further minimized by reducing the concentration of the probes.

Figure 2E:
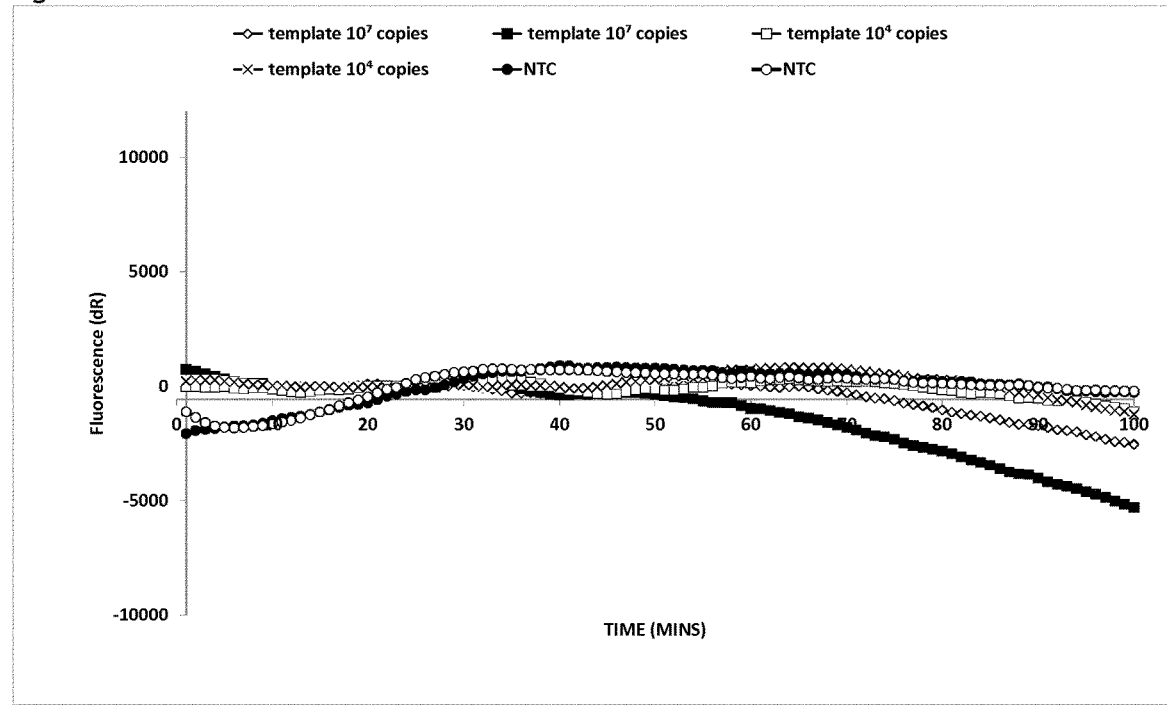

In contrast, the DNA probe (SEQ ID NO: 16) was unable to detect any amplification in presence of the target template (FIG. 2e). This is due to the fact that the presence of single strand binding proteins in the reaction results in a dramatically increase in probe signal even in the absence of the amplicon. Therefore, DNA probes were found to be unsuitable for use in methods that contain DNA binding proteins in their reagent protocol.

Example 3

Multiplex Detection of SIBA Using RNA Oligonucleotide Probes

2'-fluoro RNA probes labeled either with Cy5 and Iowa black (SEQ ID NO: 25) or with ROX and BHQ2 (SEQ ID NO: 17) were incorporated simultaneously under the strand invasion amplification reaction conditions described in Example 1. Amplification of a C. difficile target sequence (SEQ ID NO: 26) and an artificial target sequence (SEQ ID NO: 20) was detected in parallel.

Figure 3A:
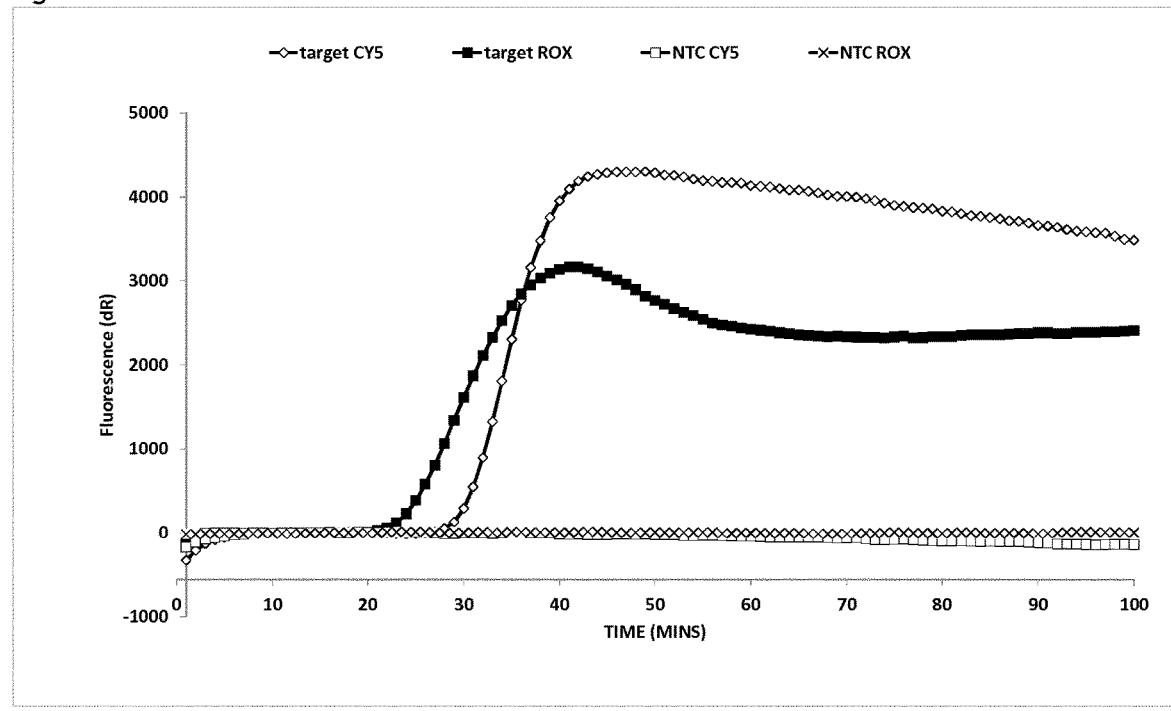
FIG. 3 shows real-time monitoring of amplification with probes containing 2'-fluoro RNA bases labeled with different fluorophores and quenchers allowing detection of multiple DNA targets. (A) Amplification and detection of two DNA targets by using a Cy5 and Iowa Black labeled probe (SC-2FLURO, SEQ ID NO: 25) for a *Clostridium difficile* target sequence and ROX and BHQ2 labeled probe (SB2-FLURO, SEQ ID NO: 17) for an artificial target sequence. X-axis: Time (minutes). Y-axis for each chart: fluorescence (arbitrary units). (B) Melt analysis of the targets after the amplification using Sybr Green I. X-axis: Temperature (degrees Centigrade). Y-axis: −(d(fluorescence)/d(temperature), arbitrary units). (C) Melt analysis of the targets after the amplification using 2'-fluoro RNA probes. X- and Y-axis as for FIG. 3(B).
Figure 3B:
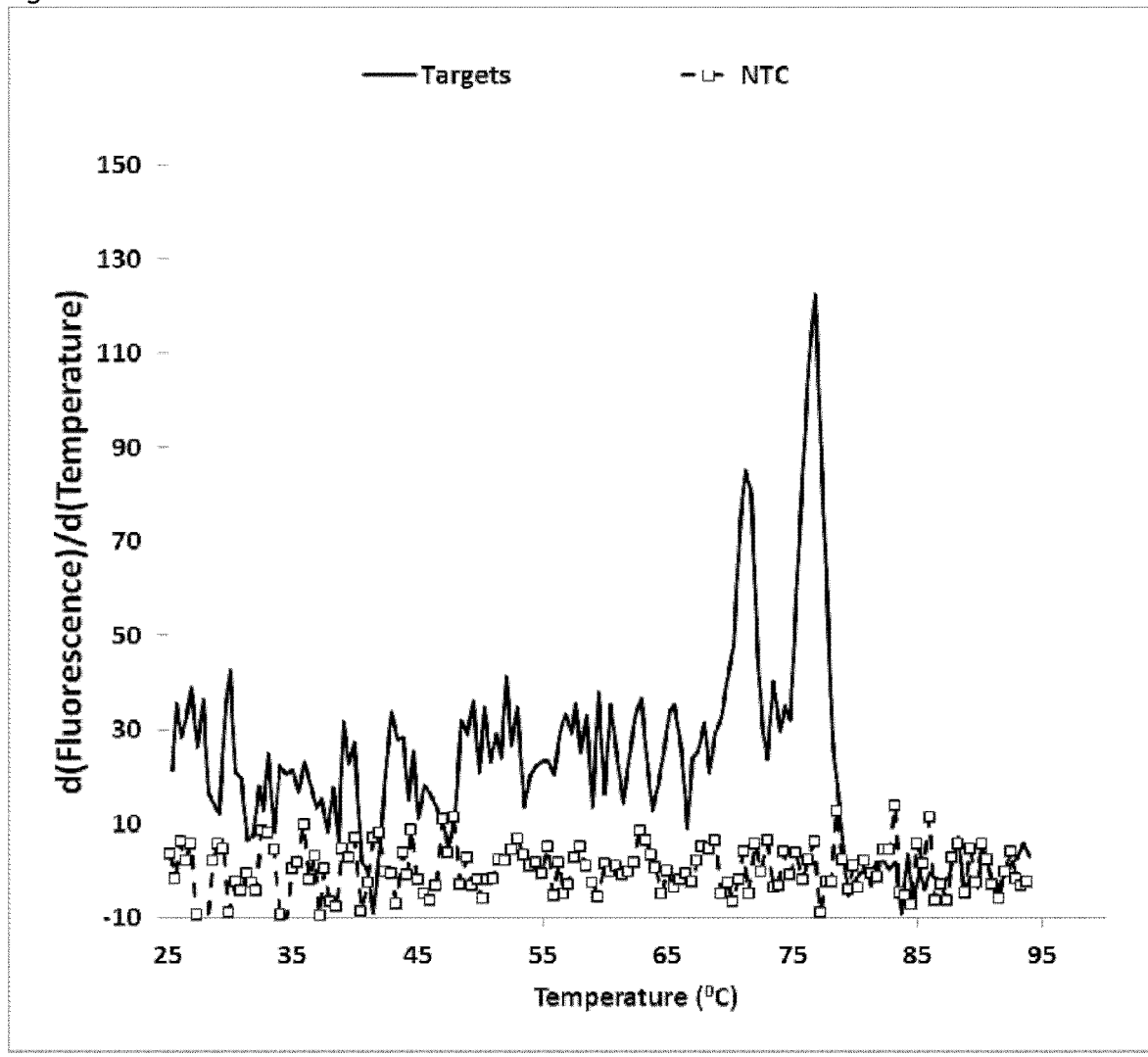
Figure 3C:
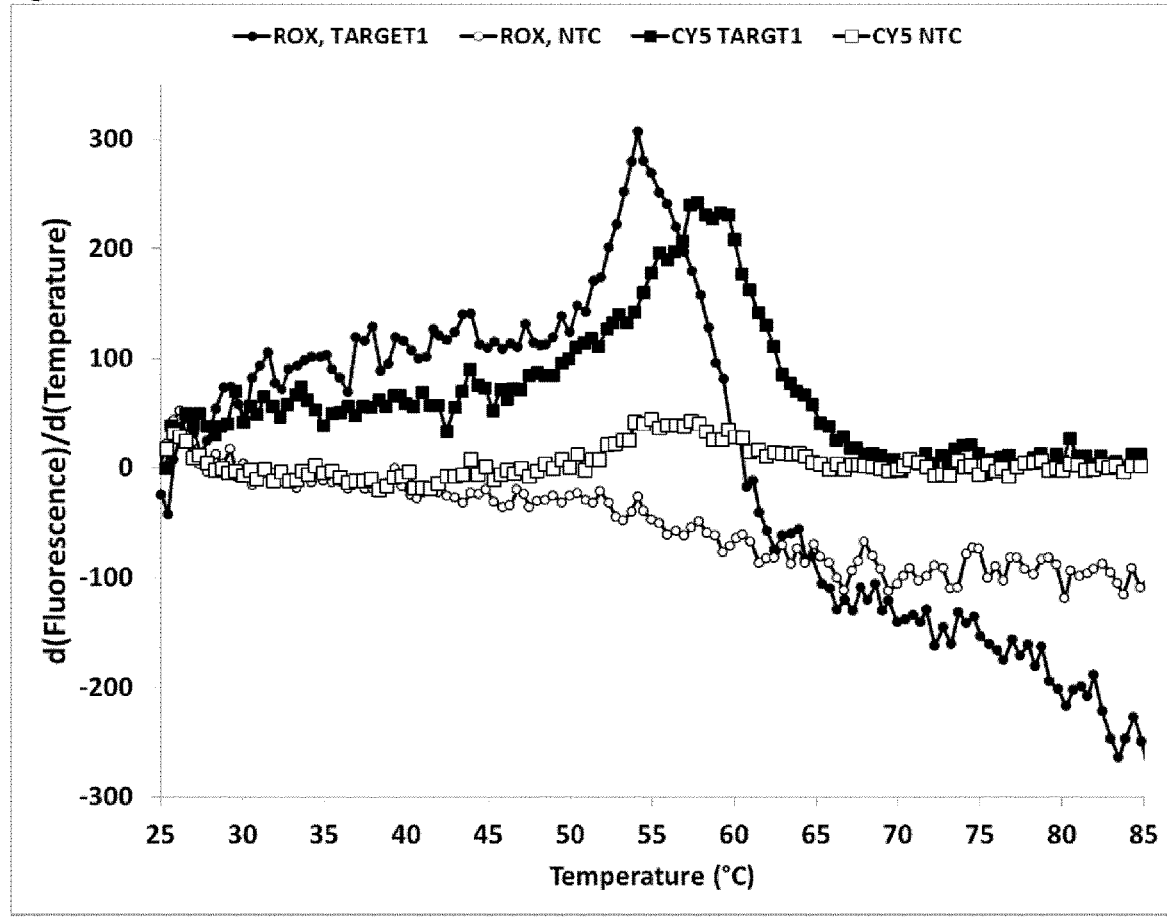

The forward primer, reverse primer and strand invasion oligonucleotide used for amplification of the target sequence from the C. difficile gene were SEQ ID NO: 21, SEQ ID NO: 22 and SEQ ID NO: 23, respectively. The forward primer, reverse primer and strand invasion oligonucleotide used for amplification of the artificial target were SEQ ID NO: 11, SEQ ID NO: 12 and SEQ ID NO: 15, respectively. The reaction was performed with 10,000 and $10^7$ copies of C. difficile genomic DNA and artificial target DNA respectively. FIG. 3a shows that real-time monitoring of the amplification of the DNA targets was achieved simultaneously by using probes containing 2'-fluoro RNA bases. 2'-fluoro RNA probes labeled with Cy5 and Iowa black (SEQ ID NO:25) was used to detect the target sequence from C. difficile, while the ROX and BHQ2 (SEQ ID NO:17) was used to detect the artificial target sequence. Melt analysis using either SYBR Green I (FIG. 3b) or 2'-fluoro RNA probes (FIG. 3c) further confirmed that both reactions were specific and occurred in the same reaction tube. 2'-fluoro RNA probes can also serve as a tool for melt analysis instead of SYBR Green, since the probes are not hydrolysed in the reactions.

Example 4

RNase H Cleavage of RNA Probes for Enhanced Signal Generation

Figure 4A:
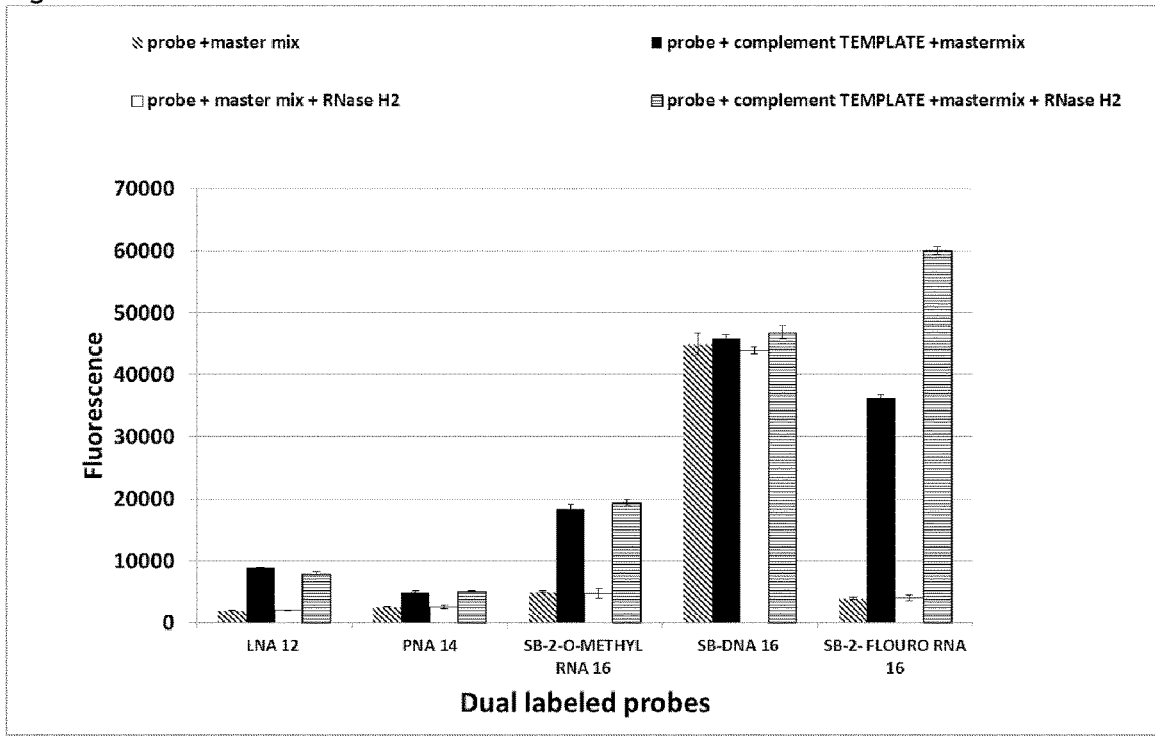
FIG. 4 shows the signal enhancement of 2'-fluoro RNA probes induced by the addition of RNase H2 cleaving the probe. (A) Dual labeled probes were incubated with complementary DNA in presence or absence of RNase H2 reagent mixture. X-axis: Left to right four conditions for each tested probe (probe with reagent mixture; probe with complementary template and reagent mixture; probe with reagent mixture and RNase H2; probe with complementary template, reagent mixture and RNase H2. Tested probes were LNA 12 (SEQ ID NO: 9), PNA 14 (SEQ ID NO: 10), SB-2'-O-methyl RNA 16 (SEQ ID NO: 32), SB-DNA 16 (SEQ ID NO:1), and SB-2'-fluoro RNA 16 (SEQ ID NO:17). Y-axis for each chart: fluorescence (arbitrary units). (B) Real-time monitoring of *C. difficile* target sequence amplification in presence or absence of RNase H2 using a 2'-fluoro RNA probe SC-2FLURO (SEQ ID NO: 24). X-axis: Time (minutes). Y-axis: fluorescence (arbitrary units).

Natural DNA, modified RNA, LNA and PNA probes were incubated in presence or absence of their complementary target template under the strand invasion DNA amplification reaction conditions described in Example 1 with or without 10 µg/ml of Thermococcus gammatolerans RNase H2. As shown in the previous experiments, all the probes (except for those containing natural DNA) produced an increase in signal when their target sequence was present (FIG. 4a). However, a further increase in signal was detected for the 2'-fluoro RNA probe (SEQ ID NO: 17) in reaction conditions where RNase H2 was present, due to cleavage of the RNA bases from the duplex of RNA-probe and target DNA. The other probes DNA (SEQ ID NO: 16), PNA (SEQ ID NO: 10), LNA (SEQ ID NO: 9) and 2'-O-methyl RNA (SEQ ID NO: 32) were not cleaved by RNase H2.

Figure 4B:
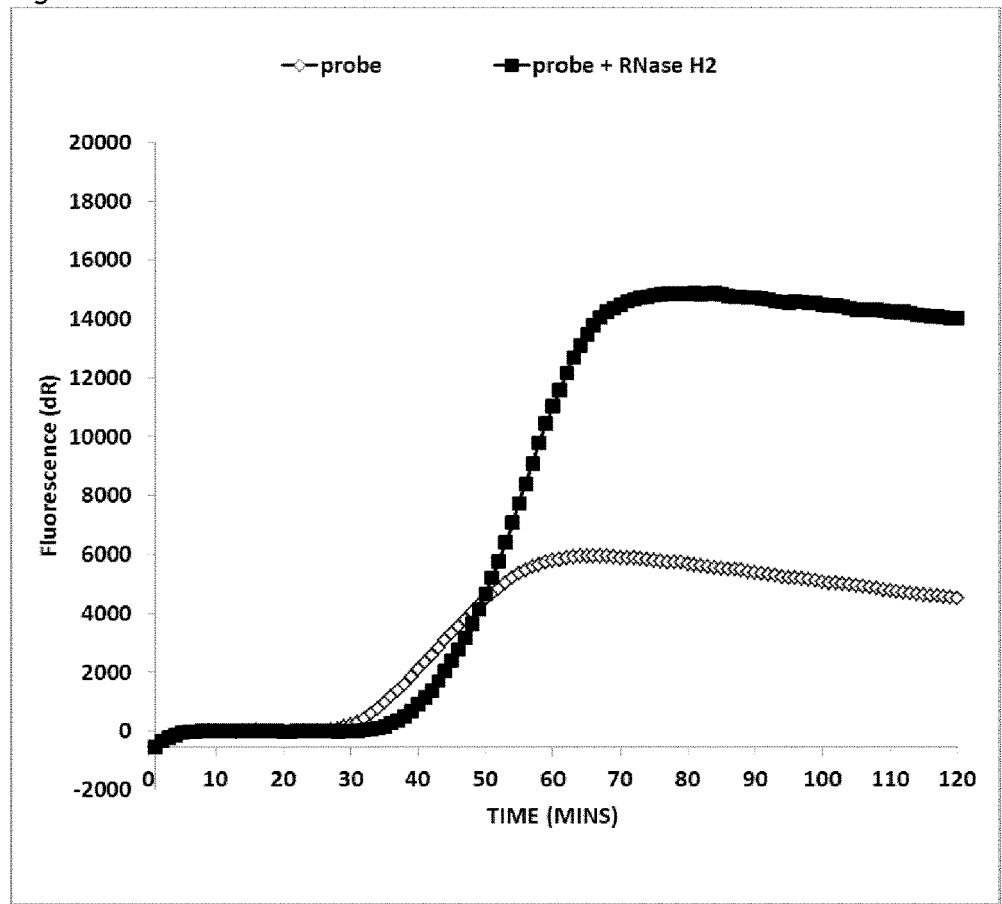

The 2'-fluoro RNA probe of SEQ ID NO: 24 was also used to detect the amplification of a target sequence from C. difficile in the presence or absence of RNase H2 under the above reaction conditions. FIG. 4b shows that RNase H2 was not a requirement for signal production from the probe. However, the presence of RNase H2 further enhanced the signal.

Example 5

Detection of Salmonella Tvphimurium by Strand-Invasion Based Amplification and an RNA Oligonucleotide Probe A 2'-fluoro RNA probe (SEQ ID NO: 30) was used to detect low copies of a target DNA. The 2'-fluoro RNA probe was incorporated under strand invasion based amplification reaction conditions described in Example 1 in an assay for detection of S. typhimurium target gene. The forward primer, reverse primer and strand-invasion oligonucleotide used for amplification were SEQ ID NO: 27, SEQ ID NO: 28 and SEQ ID NO: 29 respectively.

Figure 5:
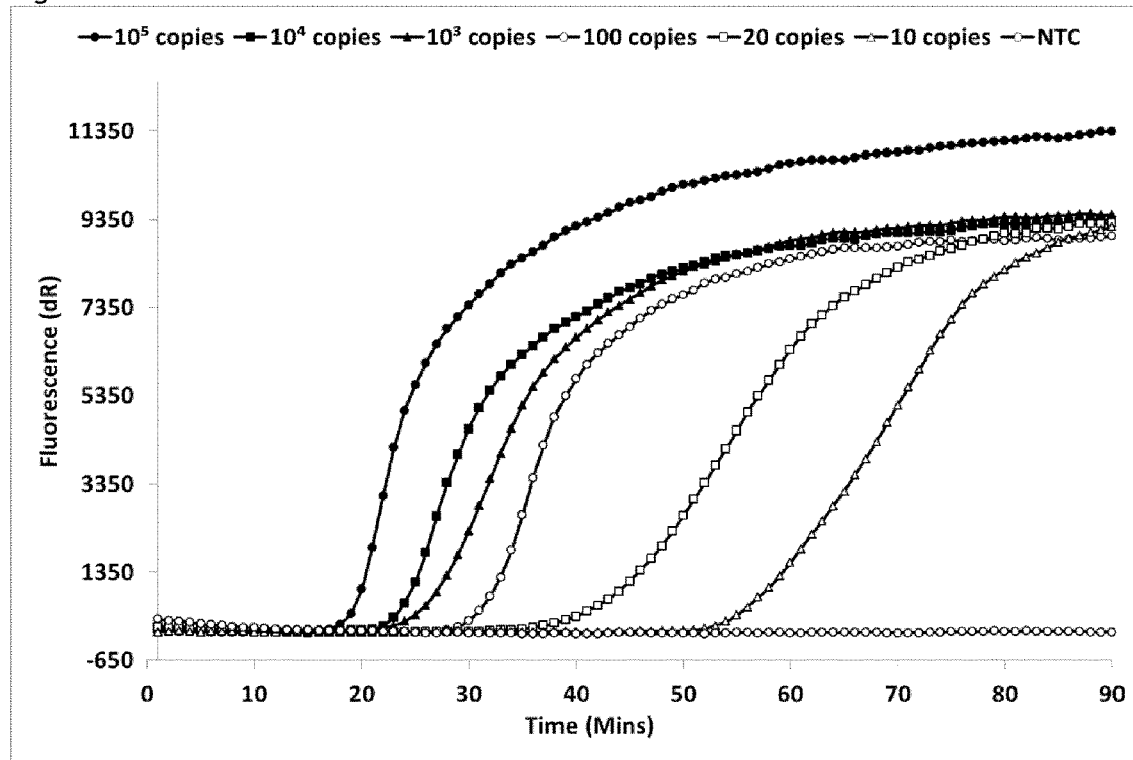
FIG. 5 shows sensitivity of a strand invasion based amplification assay for detection of *Salmonella typhimurium* using serial dilution of *S. typhimurium* genomic DNA from $10^5$ to 10 copies. Real-time monitoring of amplification using a 2'-fluoro RNA probe. Probe used was SM-2FLURO (SEQ ID NO: 30). X-axis: Time (minutes). Y-axis: Fluorescence (arbitrary units). NTC=no template control, dilutions of template shown.

The sensitivity of the test was evaluated by using a serial dilution of S. typhimurium genomic DNA from $10^5$ to 10 copies. The probe was able to detect a minimum of 10 copies of genomic DNA samples (FIG. 5). The no template control (NTC) did not produce any detectable signal confirming that the 2'-fluoro RNA probe was highly specific.

Example 6

Figure 6A:
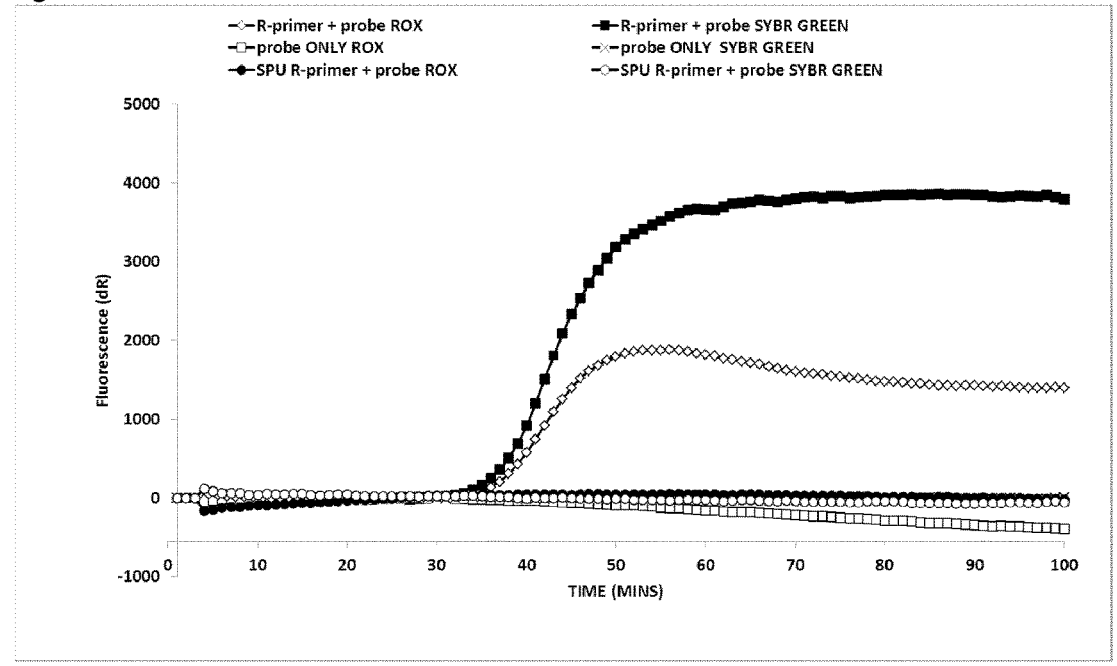
FIG. 6 shows 2'-fluoro RNA probes neither amplify nor detect the target independently of the primers (A) in the absence of RNase H2 and (B) in the presence of RNase H2. Conditions for reaction are shown for each trace. Reactions were conducted either in the presence or absence of the cognate reverse primer (SEQ ID NO: 12) or a spurious primer, SPU (SEQ ID NO: 33). Real-time monitoring of amplification was performed by detecting the ROX fluorophore from probe SB-2FLURO (SEQ ID NO: 17) or SYBR Green. X-axis: Time (minutes). Y-axis: Fluorescence (arbitrary units).
Figure 6B:
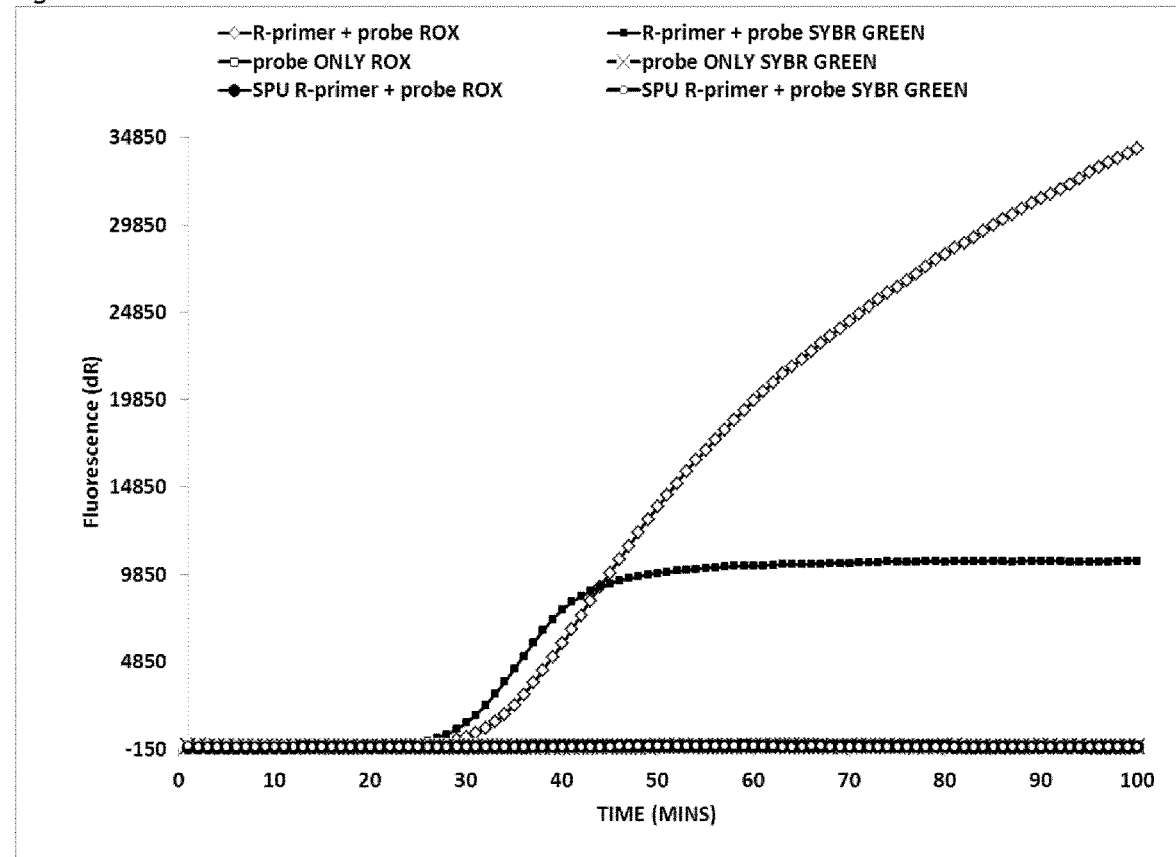

RNA Oligonucleotide Probes with Quencher Linked to 3'End do not Act as Substrates for Extension by a Polymerase The RNA probes described above were designed to overlap with the downstream region of the reverse primer and therefore might compete with the reverse primer for binding to the target sequence. It was investigated using the artificial system described in Example 2 whether the probe of SEQ ID NO: 17 could act as a substrate for priming DNA amplification. FIG. 6a shows that the probe did not act as a primer due to the presence of a quencher linked to its 3'-end. Amplification of the target sequence only occurred in presence of the complementary reverse primer (SEQ ID NO: 12). When the probe was used alone without the cognate reverse primer, or used with non-cognate or spurious reverse primer, SPU R-primer (SEQ ID NO: 33) no amplification occurred. Furthermore, no amplification was observed in the presence of RNase H2 in samples devoid of the reverse primer (FIG. 6b). This suggested that the probe was inert during amplification and only involved in the binding of the target amplicon.

Example 7

RNA Oligonucleotide with Dual Primer/Probe Function

Figure 7A:
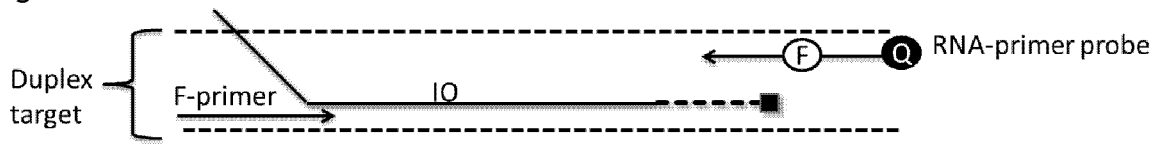
FIG. 7 shows amplification of a target DNA by strand invasion based amplification using dual function 2'-fluoro RNA primer/probes and natural DNA primers. (A) configuration of the forward primer, reverse probe-primer, strand invasion/intermediate oligonucleotide (IO) and target DNA. B) Real-time monitoring of amplification of an artificial template detected using SYBR Green. Primers used were DNA primer SB-R20 (SEQ ID NO:12), 2'-fluoro RNA primer SBFLURO1-RNA (SEQ ID NO: 13) and 2'fluoro RNA/DNA primer SBFLURO2-RNA (SEQ ID NO:14). C) Real-time monitoring of amplification of an artificial template detected using SB-R20 (SEQ ID NO: 12) or 2'-fluoro RNA probe-primer (SB-2FLURO 2, SEQ ID NO: 19) labeled with internal fluorophore (FAM) and 5'quencher. Amplification with DNA primer (SEQ ID NO: 12) detected using SYBR Green; amplification with 2'-fluoro RNA probe primer (SEQ ID NO: 19) detected via FAM channel (No SYBR Green added). NTC=no template control, dilution of template shown. X-axis: Time (minutes). Y-axis for each chart: fluorescence (arbitrary units).
Figure 7B:
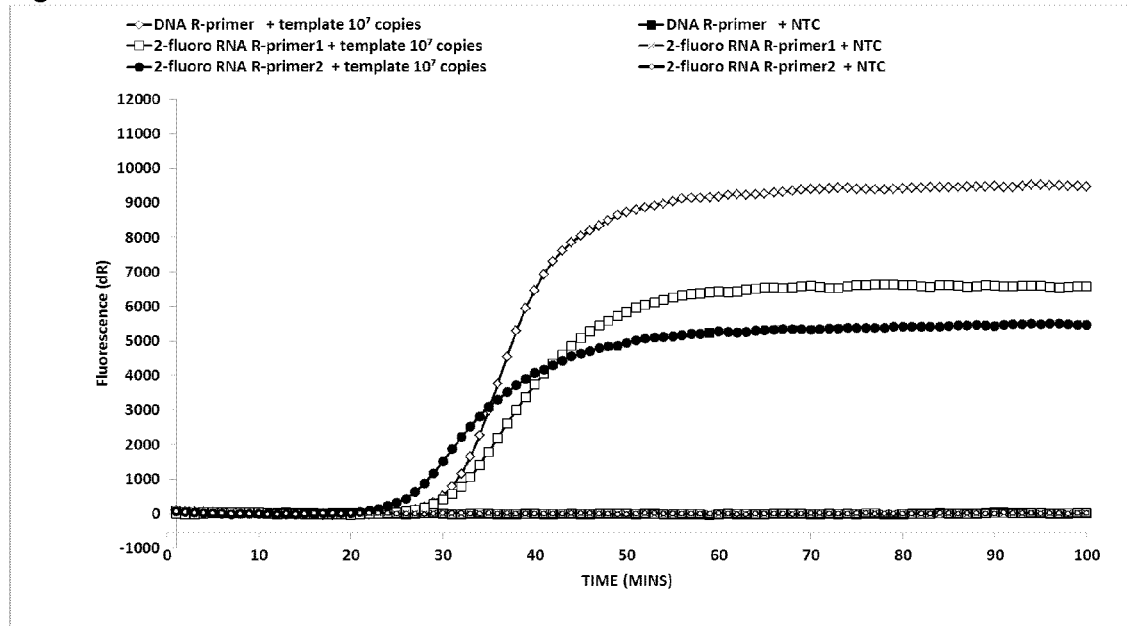

It was investigated using the artificial system described in Example 2 whether an oligonucleotide containing 2'-fluoro RNA could serve as both a probe and a primer (FIG. 7a). Part or all of the natural DNA nucleotides in the reverse primer of SEQ ID NO: 12 were replaced with 2'-fluoro RNA to generate the oligonucleotides of SEQ ID NOs: 13 and 14. These 2'-fluoro RNA primers were able to amplify an artificial target DNA with an efficiency as good as the natural DNA reverse primer (FIG. 7b). The 2'-fluoro RNA primer retaining a few natural DNA bases at the 3' end (SEQ ID NO: 14) was slightly more efficient.

Figure 7C:
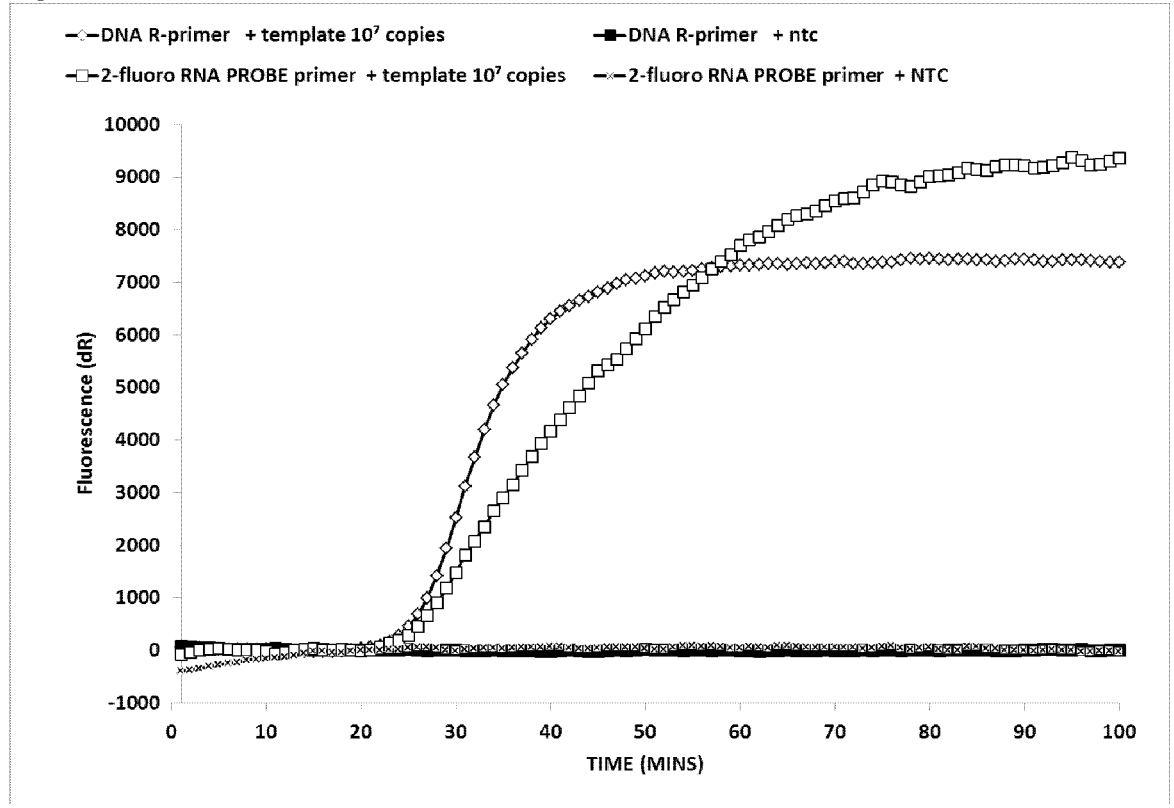

It was then reasoned that a fluorophore and a quencher might be added to the 2'-fluoro RNA primer to provide a probe function so long as the 3'-end was free to extend the target sequence. It was further postulated that such a configuration would still be resistant to interference by DNA binding proteins with the probe signal and therefore still allow for specific detection of amplification. The 2'-fluoro RNA primer was labeled with an internal fluorophore and 5' quencher (SEQ ID NO 19). FIG. 7c shows that SEQ ID NO: 19 was able to amplify and detect artificial target DNA (SEQ ID NO: 20) in a strand invasion based amplification reaction.

Example 8

Affinity of Chimeric DNA-RNA Dual Labeled Probes for DNA Binding Proteins

The ability to provide resistance to DNA binding proteins by modifying the sequence of a natural DNA probe to incorporate in part RNA or modified RNA bases was investigated. The concentrations of dual labeled probes, UvsX and T4-gp32 were identical to those used in Example 1.

FIG. 8 shows that dual labeled probes containing a mixture of DNA and RNA (SEQ ID NOs: 35, 36, 37) or DNA and 2'-fluoro RNA (SEQ ID NOs: 38, 39, 40) or DNA and 2'-O-methyl RNA (SEQ ID NOs: 41, 42, 43), bases also displayed resistance to the DNA binding proteins UvsX and T4-gp32. Results are shown as the fold increase in fluorescence as a result of addition of UvsX or T4-gp32. The degree of resistance was predominantly dependent on the amount of RNA bases present in the dual labeled probes. The resistance of dual labeled probes to DNA binding proteins increased as the amount of RNA bases present in the probes increased.

Figure 8A:
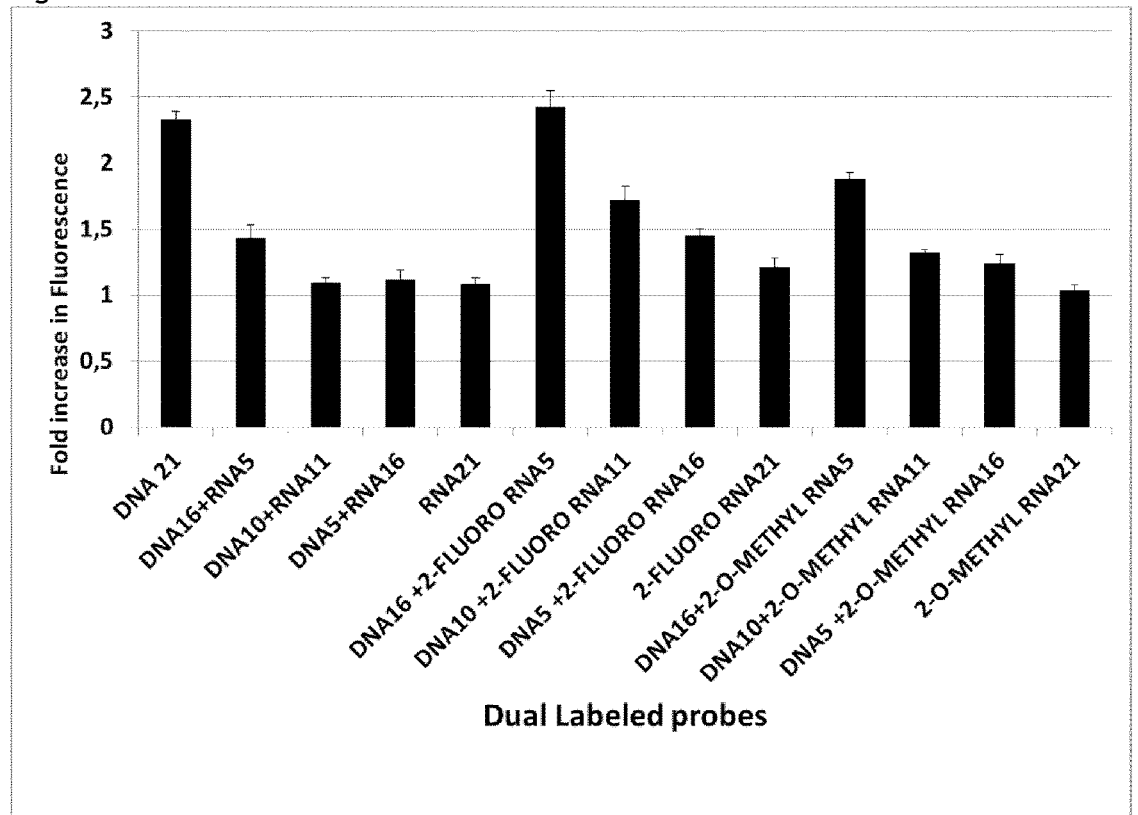
FIG. 8 shows the effect of recombinase UvsX and single strand binding protein T4-gp32 on signal from dual-labeled chimeric probes having DNA and RNA bases (DNA/RNA or DNA/2'-fluoro RNA or DNA/2'-O-methyl RNA) in absence of a complementary template. A) effect of UvsX. B) effect of T4-gp32. C) Additional UvsX assay with a further series of probes. D) Additional T4 gp32 assay with a further series of probes. Probes tested were DNA 21 (SEQ ID NO: 2), DNA 16+RNA5 (SEQ ID NO: 35), DNA 10+RNA 11 (SEQ ID NO: 36), DNA5+RNA16 (SEQ ID NO: 37), RNA21 (SEQ ID NO: 4), DNA16+2-FLUORO RNA5 (SEQ ID NO: 38), DNA10+2-FLUORO RNA11 (SEQ ID NO: 39), DNA 5+2-FLUORO RNA 16 (SEQ ID NO: 40), 2-FLUORO RNA21 (SEQ ID NO: 8), DNA16+2-O-METHYL RNA5 (SEQ ID NO: 41), DNA10+2-O-METHYL RNA11 (SEQ ID NO: 42), DNA5+2-O-METHYL RNA16 (SEQ ID NO: 43), 2-O-METHYL RNA21 (SEQ ID NO: 6), DNA20+RNA1 (SEQ ID NO: 45), DNA19+RNA2 (SEQ ID NO: 46), DNA18+RNA3 (SEQ ID NO: 47); DNA17+RNA4 (SEQ ID NO:48). Y-axis: fold increase in fluorescence (fluorescence in presence of UvsX or T4-gp32 divided by fluorescence in absence of UvsX or T4-gp32), arbitrary units.
Figure 8B:
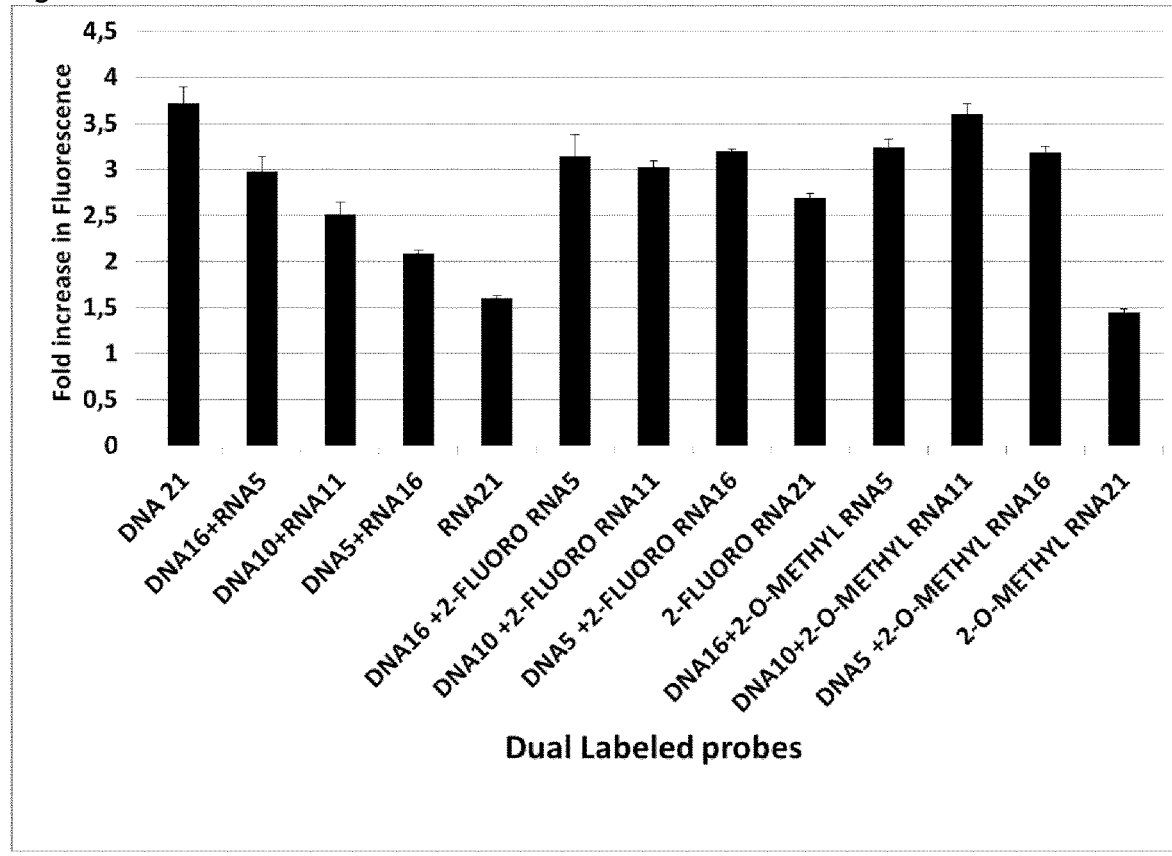

UvsX was incubated with 21 base dual labeled probes containing different ratios of DNA-RNA, DNA-2'-fluoro RNA and 2'-O-methyl RNA (FIG. 8a). In all cases, 21 base dual labeled probes containing 5 RNA or 2'-fluoro RNA or 2'-O-methyl RNA bases and 15 DNA bases were more resistant to UvsX than a 21 base dual labeled probe containing only DNA bases. A similar experiment was conducted with T4-bacteriophage gp32 (single strand binding protein) (FIG. 8b). Resistance to DNA binding proteins was again predominantly dependent on the amount of RNA bases presence in the dual labeled probes. A 21 base dual labeled probes containing 5 RNA or 2'-fluoro RNA or 2'-O-methyl RNA bases and 15 DNA bases was sufficient to display resistance to T4-gp32. Therefore chimeric DNA-RNA or DNA-2'-fluoro-RNA or DNA-2'-O-methyl RNA dual labeled probes are also suitable for use in reactions containing DNA binding proteins.

Figure 8C:
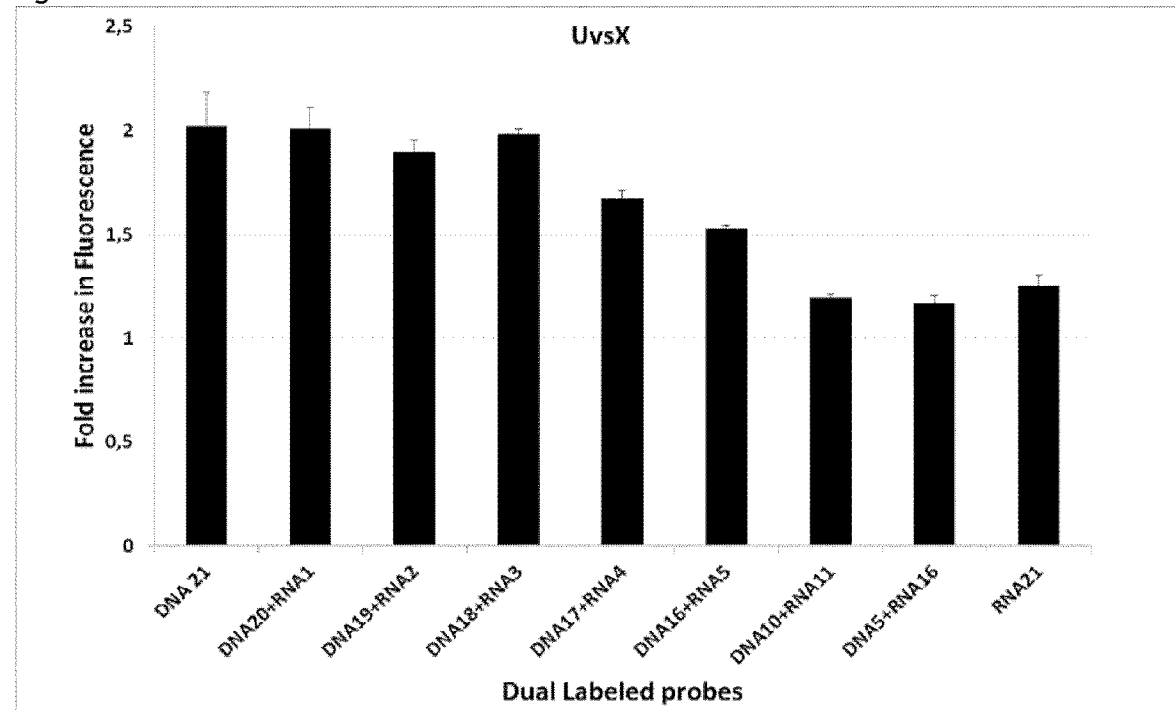
Figure 8D:
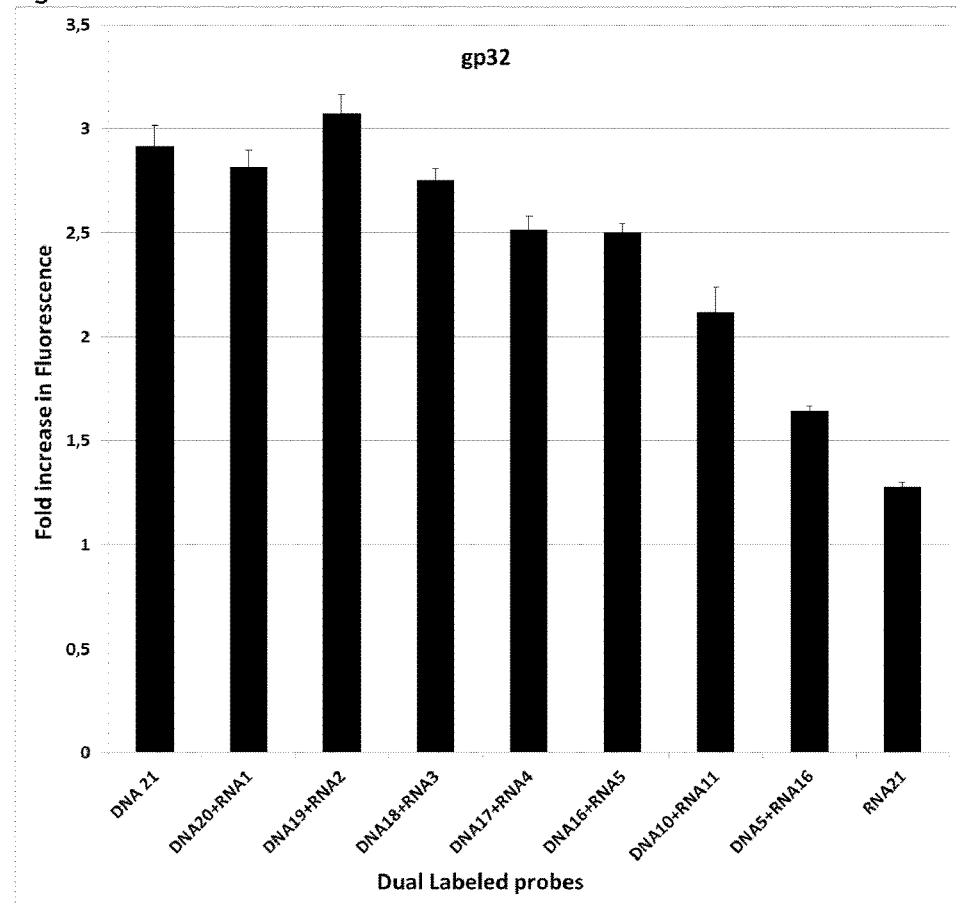

The relationship between the number of RNA bases included in the chimeric probe and the resistance to disruption of probe signal by proteins capable of binding single-stranded DNA was investigated further. FIG. 8c shows results for incubation of UvsX with an additional series of 21-based dual labelled probes containing different rations of DNA-RNA. FIG. 8d shows results with the same series of probes and incubation with gp32. The assays were carried out as described in Example 1. It was found that a consistent reduction in interference with probe signal was observed where at least about 20% of the bases in the DNA probe were substituted for RNA bases (see for example the probe DNA 17+RNA 4).

The invention claimed is:

1. A method for detection of a target nucleic acid sequence in a sample in the presence of at least one recombinase comprising contacting said sample with at least one oligonucleotide probe comprising a fluorophore, a quencher and a region complementary to said target nucleic acid sequence, wherein the sequence of said oligonucleotide probe comprises at least 20% RNA nucleotides, modified RNA nucleotides and/or PNA nucleotides, wherein the probe comprises one or more modified RNA nucleotides selected from 2'-fluoro ribonucleotides, 2'-O-methyl ribonucleotides and/or LNA ribonucleotides, wherein said oligonucleotide probe is single stranded, wherein the method further comprises strand invasion based amplification of said target nucleic acid sequence under isothermal conditions promoting amplification of said target nucleic acid sequence comprising contacting said sample with:
 (i) at least one upstream primer and at least one downstream primer, each comprising a region complementary to said target nucleic acid sequence, and
 (ii) a strand invasion oligonucleotide comprising a region complementary to said target nucleic acid sequence;
wherein the strand invasion oligonucleotide renders at least a portion of the target nucleic acid sequence single-stranded to allow the binding of the at least one upstream primer and at least one downstream primer and said probe;
and wherein said recombinase is used for strand invasion of said target nucleic acid sequence;
further wherein the target nucleic acid sequence is double stranded.

2. A method according to claim 1, where said oligonucleotide probe is capable of priming amplification of said target nucleic acid sequence and functions as said at least one upstream or downstream primer.

3. A method according to claim 1, wherein said recombinase is selected from UvsX or RecA.

4. A method according to claim 1, wherein said oligonucleotide probe comprises the sequence of SEQ ID NO: 24, 25 or 30 or a variant of any thereof.

5. A method according to claim 1, where the sequence of said oligonucleotide probe comprises at least 20% 2'-fluoro ribonucleotides, 2'-O-methyl ribonucleotides, and/or LNA ribonucleotides.

6. A method according to claim 1, wherein said upstream and downstream primers are less than 25 nucleotides in length, and have 5' binding sites of at least 45 nucleotides apart on the target sequence.

7. A method according to claim 1, wherein the sequence of said oligonucleotide probe comprises at least 20% modified RNA nucleotides and/or PNA nucleotides or comprises from 20% to 60% RNA nucleotides.

8. A method according to claim 1, wherein the sequence of said oligonucleotide probe comprises at least 50% 2'-fluoro ribonucleotides, 2'-O-methyl ribonucleotides, or LNA nucleotides.

9. A method according to claim 1, wherein the sequence of said oligonucleotide probe comprises at least 50% 2'fluoro ribonucleotides or LNA nucleotides.

10. A method according to claim 1, wherein the sequence of said oligonucleotide probe comprises at least 50% LNA nucleotides.

11. A method according to claim 10, wherein said oligonucleotide probe is of 15-25 nucleotides in length.

12. A method according to claim 1, wherein said oligonucleotide probe comprises a region of secondary structure whose conformation is altered on binding to the target nucleic acid sequence.

13. A method according to claim 1, wherein said method does not comprise contacting said sample with RNase H.

14. A method for measuring for a target nucleic acid sequence from a pathogen in a sample from a subject, comprising carrying out a method as defined in claim 1 in a sample from a subject suspected of having the target nucleic acid sequence from said pathogen.

* * * * *